United States Patent [19]
Ward et al.

[11] Patent Number: 5,531,776
[45] Date of Patent: Jul. 2, 1996

[54] NON-INVASIVE AORTIC IMPINGEMENT AND CORE AND CEREBRAL TEMPERATURE MANIPULATION METHOD

[75] Inventors: Kevin R. Ward; Charles G. Brown; Roger R. Dzwonczyk, all of Columbus, Ohio

[73] Assignee: The Ohio State University, Columbus, Ohio

[21] Appl. No.: 266,201

[22] Filed: Jun. 27, 1994

Related U.S. Application Data

[63] Continuation-in-part of Ser. No. 126,542, Sep. 24, 1993.

[51] Int. Cl.$^6$ .................................................. A61F 7/12
[52] U.S. Cl. ........................ 607/105; 607/113; 128/898; 600/16; 606/27; 606/21
[58] Field of Search ............................ 607/96, 104, 105, 607/106, 113–124, 133; 128/672, 668, 673, 677, 736, 897, 898, DIG. 27; 606/20, 21, 27; 600/16–18

[56] References Cited

U.S. PATENT DOCUMENTS

| | | | |
|---|---|---|---|
| 3,425,419 | 2/1969 | Dato | 607/106 |
| 4,090,518 | 5/1978 | Elam . | |
| 4,198,963 | 4/1980 | Barkalow et al. . | |
| 4,640,298 | 2/1987 | Pless et al. . | |
| 4,706,688 | 11/1987 | Michael et al. . | |
| 4,960,133 | 10/1990 | Hewson . | |
| 5,056,532 | 10/1991 | Hull et al. . | |
| 5,077,667 | 12/1991 | Brown et al. . | |
| 5,151,100 | 9/1992 | Abele et al. | 607/113 |
| 5,170,803 | 12/1992 | Hewson et al. . | |
| 5,179,952 | 1/1993 | Buinevicius et al. . | |
| 5,188,602 | 2/1993 | Nichols | 607/105 |
| 5,191,885 | 3/1993 | Bilof et al. . | |
| 5,197,491 | 3/1993 | Anderson et al. . | |
| 5,261,411 | 11/1993 | Hughes | 128/898 |
| 5,398,692 | 3/1995 | Hickey | 128/673 |
| 5,431,696 | 7/1995 | Atlee, III | 128/642 |
| 5,437,633 | 8/1995 | Manning | 128/898 |

OTHER PUBLICATIONS

Product brochure entitled "EsoThor™—Esophageal—Thoracic Technology Min-Invasive A-V Sequential Pacing," published by Brunswick Biomedical Technologies, date unknown.

Brown, Charles G., M.D. et al., "A Comparison of Standard-Dose and High-Dose Epinephrine in Cardiac Arrest Outside the Hospital," *New England Journal of Medicine*, vol. 327, Oct. 8, 1992, pp. 1051–1055.

Manning, James E., M.D. et al., "Selective Aortic Arch Perfusion During Cardiac Arrest: A New Resuscitation Technique," *Annals of Emergency Medicine*, Sep., 1992, pp. 1058–1065.

Berg, Robert A., M.D., F.A.A.P. et al., "High-Dose Epinephrine Results in Greater Early Mortality After Resuscitation From Prolonged Cardiac Arrest in Pigs: A Prospective, Randomized Study," *Critical Care Medicine*, vol. 22, No. 2, Feb., 1994, pp. 282–290.

Mattox, Kenneth L., M.D. et al., "Prospective MAST Study in 911 Patients," *The Journal of Trauma*, vol. 29, No. 8, Aug., 1989, pp. 1104–1112.

(List continued on next page.)

*Primary Examiner*—William E. Kamm
*Assistant Examiner*—Kennedy J. Schaetzle
*Attorney, Agent, or Firm*—Price, Heneveld, Cooper, DeWitt & Litton

[57] ABSTRACT

A method of non-invasively occluding the descending thoracic aorta to a desired extent in order to enhance cerebral and myocardial perfusion or the like, and/or of manipulating core and cerebral temperature of a patient, wherein a device is extended into the patient's esophagus and manipulated to selectively displace a wall of the esophagus toward the descending thoracic aorta to thereby at least partially occlude the latter, and/or to exchange heat between a device positioned in the patient's esophagus and a proximately located thoracic vessel in order to increase or decrease the temperature of blood flowing in such vessel.

32 Claims, 9 Drawing Sheets

OTHER PUBLICATIONS

Eisenberg, Mickey S., M.D., PhD et al., "Cardiac Arrest and Resuscitation: A Tale of 29 Cities," *Annals of Emergency Medicine*, Feb., 1990, pp. 179–186.

Eisenberg, Mickey S., M.D., PhD et al., "Long–Term Survival After Out–of Hospital Cardiac Arrest," *The New England Journal of Medicine*, vol. 306, No. 22, Jun. 3, 1982, pp. 1340–1343.

Becker, Lance B., M.D. et al., "Outcome of CPR in a Large Metropolitan Area—Where are the Survivors?," *Annals of Emergency Medicine*, Apr., 1991, pp. 355–361.

Safar, Peter, M.D., "Resuscitation From Clinical Death: Pathophysiologic Limits and Therapeutic Potentials," *Critical Care Medicine*, vol. 16, No. 10, Oct., 1988, pp. 923–941.

Safar, Peter, M.D., "Cerebral Resuscitation After Cardiac Arrest: Research Initiatives and Future Directions," *Annals of Emergency Medicine*, Feb., 1993, pp. 324–349.

Wolfson, Jr., Sidney K. et al., "Dynamic Heterogeneity of Cerebral Hypoperfusion After Prolonged Cardiac Arrest in Dogs Measured by the Stable Xenon/CT Technique: a Preliminary Study," *Resuscitation*, 23 (1992), pp. 1–20.

Brown, Charles G., M.D. et al., "The Effect of Norepinephrine Versus Epinephrine on Regional Cerebral Blood Flow During Cardiopulmonary Resuscitation," *American Journal of Medicine*, vol. 7, No. 3, May, 1989, pp. 278–282.

Brown, Charles G., M.D., FACEP et al., "Comparative Effect of Graded Doses of Epinephrine on Regional Brain Blood Flow During CPR in a Swine Model," *Annals of Emergency Medicine*, Oct., 1986, pp. 1138–1144.

Robinson, Linda A., M.D. et al., "The Effect of Norepinephrine Versus Epinephrine on Myocardial Hemodynamics During CPR," *Annals of Emergency Medicine*, Apr., 1989, pp. 336–340.

Sharff, Jeffrey A., M.D., "Effect of Time on Regional Organ Perfusion During Two Methods of Cardiopulmonary Resuscitation," *Annals of Emergency Medicine* (Part 1), Sep., 1984, pp. 649–656.

Schleien, Charles L., M.D., "Effect of Epinephrine on Cerebral and Myocardial Perfusion in an Infant Animal Preparation of Cardiopulmonary Resuscitation," *Circulation*, vol. 73, No. 4, Apr., 1986, pp. 806–817.

Kuboyama, Kazutoshi, M.D. et al., "Delay in Cooling Negates the Beneficial Effect of Mild Resuscitative Cerebral Hypothermia After Cardiac Arrest in Dogs: A Prospective, Randomized Study," *Critical Care Medicine*, vol. 21, No. 9, Sep., 1993, pp. 1348–1358.

Leonov, Yuval, M.D. et al., "Hypertension With Hemodilution Prevents Multifocal Cerebral Hypoperfusion After Cardiac Arrest in Dogs," *Stroke*, vol. 23, No. 1., Jan., 1992, pp. 45–53.

Sterz, Fritz, M.D. et al., "Hypertension With or Without Hemodilution After Cardiac Arrest in Dogs," *Stroke*, vol. 21, No. 8, Aug., 1990, pp. 1178–1184.

Bavaria, Joseph E., M.D. et al., "Myocardial Oxygen Utilization After Reversible Global Ischemia," *J Thorac Cardiovasc Surg*, vol. 100, No. 2, Aug., 1990, pp. 210–220.

Ballantyne, Christie M., M.d. et al., "Delayed Recovery of Severely 'Stunned' Myocardium with the Support of a Left Ventricular Assist Device After Coronary Artery Bypass Graft Surgery," *JACC*, vol. 10, No. 3, Sep., 1987, pp. 710–7112.

Cutler, Bruce, "The Intraaortic Balloon and Counterpulsation," *Intensive Care Medicine*, Second Edition, 1991, pp. 130–140.

Billhardt, Roger A., M.D. et al., "Cardiogenic and Hypovolemic Shock," *Medical Clinics of North America*, vol. 70, No. 4, Jul., 1986, pp. 853–874.

Swenson, Robert D., M.D. et al., "Hemodynamics in Humans During Conventional and Experimental Methods of Cardiopulmonary Resuscitation," *Circulation*, vol. 78, No. 3, Sep., 1988, pp. 630–639.

Redberg, Rita F., M.D. et al., "Physiology of Blood Flow During Cardiopulmonary Resuscitation/A Transesophageal Echocardiographic Study," *Circulation*, vol. 88, No. 2, Aug., 1993, pp. 534–542.

Otto, Charles W., "Current Concepts in Cardiopulmonary Resuscitation," *Seminars in Anesthesia*, vol. IX, No. 3, Sep., 1990, pp. 169–181.

Babbs, Charles F., M.D., PhD, "New Versus Old Theories of Blood Flow During CPR," *Critical Care Medicine*, vol. 8, No. 3, Mar., 1980, pp. 191–195.

Niemann, James T., M.D., "Differences in Cerebral and Myocardial Perfusion During Closed–Chest Resuscitation," *Annals of Emergency Medicine* (Part 2), Sep., 1984, pp. 849–853.

Niemann, James T., M.D. et al., "Predictive Indices of Successful Cardiac Resuscitation After Prolonged Arrest and Experimental Cardiopulmonary Resuscitation," *Annals of Emergency Medicine*, Jun., 1985, pp. 521–528.

Paradis, Norman A., M.D. et al., "Coronary Perfusion Pressure and the Return of Spontaneous Circulation in Human Cardiopulmonary Resuscitation," *JAMA*, vol. 263, No. 8, Feb. 23, 1990, pp. 1106–1113.

Martin, Gerard B., M.D. et al., "Aortic and Right Atrial Pressures During Standard and Simultaneous Compression and Ventilation CPR in Human Beings," *Annals of Emergency Medicine*, Feb., 1986, pp. 125–130.

Niemann, James T., M.D. et al., "Coronary Perfusion Pressure During Experimental Cardiopulmonary Resuscitation," *Annals of Emergency Medicine*, Mar., 1982, pp. 127–131.

DeBehnke, Daniel J., M.D. et al., "Comparison of Standard External CPR, Open–Chest CPR, and Cardiopulmonary Bypass in a Canine Myocardial Infarct Model," *Annals of Emergency Medicine*, Jul., 1991, pp. 754–760.

Niemann, James T., "Alternatives to Standard CPR," *Cardiopulmonary Resuscitation*, 1989, pp. 103–116.

Martin, Gerard B., M.D. et al., "Cardiopulmonary Bypass vs CPR as Treatment for Prolonged Canine Cardiopulmonary Arrest," *Annals of Emergency Medicine*, Jun., 1987, pp. 628–636.

Emerman, Charles L., M.D. et al., "Hemodynamic Effects of the Intra–aortic Balloon Pump During Experimental Cardiac Arrest," *American Journal of Emergency Medicine*, vol. 7, No. 4., Jul., 1989, pp. 378–383.

Bircher, Nicholas, AB et al., "A Comparison of Standard, 'MAST'–Augmented, and Open–Chest CPR in Dogs," *Critical Care Medicine*, vol. 8, No. 3., Mar., 1980, pp. 147–152.

Cohen, Todd J., M.D. et al., "A comparison of Active Compression–Decompression Cardiopulmonary Resuscitation With Standard Cardiopulmonary Resuscitation for Cardiac Arrests Occurring in the Hospital," *The New Englad Journal of Medicine*, vol. 329, No. 26, Dec., 23, 1993, pp. 1918–1921.

Safar, Peter, M.D. et al., "Emergency Cardiopulmonary Bypass for Resuscitation From Prolonged Cardiac Arrest," *American Journal of Emergency Medicine*, vol. 8, No. 1., Jan., 1990, pp. 55–67.

Griffith, Robert F. et al., "A Comparison of Three Non-Invasive Measurements for Coronary Perfusion Pressure and Prediction of Return of Spontaneous Circulation During Cardiopulmonary Resuscitation," *Critical Care Medicine*, Apr. 1993.

Buckman, Jr., Robert et al., "Minimally-Invasive Direct Cardiac Massage: Systemic Blood Flow," *Critical Care Medicine*, Apr., 1993.

Halperin, Henry R., M.D. et al., "Vest Inflation Without Simultaneous Ventilation During Cardiac Arrest in Dogs: Improved Survival From Prolonged Cardiopulmonary Resuscitation," *Circulation*, vol. 74, No. 6, Dec., 1986, pp. 1407–1415.

"A Preliminary Study of Cardiopulmonary Resuscitation by Circumferential Compression of the Chest With Use of a Pneumatic Vest," *The New England Journal of Medicine*, vol. 329, No. 11, Sep. 9, 1993, pp. 762–768.

Halperin, Henry R., M.D. et al., "Cardiopulmonary and Critical Care: New Cariopulmonary Resuscitation Techniques," *Abstracts From the 65th Scientific Sessions, Circulation*, Supplement I, vol. 86, No. 4, Oct., 1992, pp. I-233.–I-235.

Cohen, Todd J., M.D. et al., "Active Compression–Decompression/A New Method of Cardiopulmonary Resuscitation," *JAMA*, vol. 267, No. 21, Jun. 3, 1992, pp. 2916–2923.

Alexander, Raymond H., M.D., FACS et al., "Chapter 3: Shock," *Advanced Trauma Life Support Program for Physicians*, Fifth Edition, 1993.

Moore, John B. et al., "Chapter 12: Emergency Department Thoracotomy," *Trauma*, Second Edition, 1988, pp. 181–193.

Kowalenko, Terry, M.D. et al., "Improved Outcome With Hypotensive Resuscitation of Uncontrolled Hemorrhagic Shock in a Swine Model," *The Journal of Trauma*, vol. 33, No. 3, Sep., 1992, pp. 349–353.

Stern, Susan A., M.D. et al., "Effect of Blood Pressure on Hemorrhage Volume and Survival in a Near-Fatal Hemorrhage Model Incorporating a Vascular Injury," *Annals of Emergency Medicine*, Feb., 1993, pp. 155–163.

Low, Ronald B., M.D. et al., "Preliminary Report on the Use of the Percluder® Occluding Aortic Balloon in Human Beings," *Annals of Emergency Medicine*, Dec., 1986, pp. 1466–1469.

Gupta, Bhupendra K., M.D. et al., "The Role of Intra-aortic Balloon Occlusion in Penetrating Abdominal Trauma," *The Journal of Trauma*, vol. 29, No. 8, Jun., 1989, pp. 861–865.

Landreneau, Rodney J., M.D. et al., "Splanchnic Blood Flow Response to Intraaortic Balloon Pump Assist of Hemorrhagic Shock[1]," *Journal of Surgical Research*, vol. 51, No. 4, Oct., 1991, pp. 281–287.

Tisherman, Samuel A., M.D. et al., "Therapeutic Deep Hypothermic Circulatory Arrest in Dogs: A Resuscitation Modality for Hemorrhagic Shock With 'Irreparable' Injury," *The Journal of Trauma*, vol. 30, No. 7, Jul., 1990, pp. 836–847.

Mabey, Brent Edward, "Chapter 70: Abdominal Aortic Aneurysm, *Emergency Medicine/Concepts and Clinical Practice*," Third Edition, vol. II, pp. 1372–1383.

White, Robert J., M.D., PhD et al., "The Diagnosis and Initial Management of Head Injury," *The New England Journal of Medicine*, vol. 327, No. 21, Nov. 19, 1992, pp. 1507–1511.

Gentleman, Douglas et al., "Guidelines for Resuscitation and Transfer of Patients With Serious Head Injury," *BMJ*, vol. 307, Aug. 28, 1993, pp. 547–552.

Hariri, Robert J., M.D., PhD et al., "Traumatic Brain Injury, Hemorrhagic Shock, and Fluid Resuscitation: Effects on Intracranial Pressure and Brain Compliance," *J. Neurosurg*, vol. 79, Sep., 1993, pp. 421–427.

Fulton, Robert L., M.D. et al., "Brain Injury Causes Loss of Cardiovascular Response to Hemorrhagic Shock," *Journal of Investigative Surgery*, vol. 6, pp. 117–131.

Rosner, Michael J., M.D. et al., "Cerebral Perfusion Pressure Management in Head Injury," *The Journal of Trauma*, vol. 30, No. 8, Aug., 1990, pp. 933–941.

Marion, Donald W., M.D. et al., "The Use of Moderate Therapeutic Hypothermia for Patients With Severe Head Injuries: A Preliminary Report," *J. Neurosurg.*, vol. 79, Sep. 1993, pp. 354–362.

Marion, Donald W., M.D. et al., "Acute Regional Cerebral Blood Flow Changes Caused by Severe Head Injuries," *J. Neurosurg.*, vol. 74, Mar., 1991, pp. 407–414.

Feldman, James A., M.D., F.A.C.E.P. et al., "Resuscitation Fluid for a Patient With Head Injury and Hypovolemic Shock," *The Journal of Emergency Medicine*, vol. 9, Feb. 23, 1991, pp. 465–468.

Shackford, Steven R., M.D., F.A.C.S. et al., "The Effects of Aortic Crossclamping and Resuscitation on Intracranial Pressure, Cerebral Blood Flow, and Cerebral Water Content in a Model of Focal Brain Injury and Hemorrhagic Shock," *The Journal of Trauma*, vol. 30, No. 7, Jul., 1990, pp. 768–775.

Yarbrough, Barry E. et al., "Heat–Related Illnesses," *Management of Wilderness and Environmental Emergencies*, Second Edition, 1989, pp. 119–143.

Danzyl, Daniel F. et al., "Accidental Hypothermia," *Management of Wilderness and Environmental Emergencies*, Second Edition, 1989, pp. 35–76.

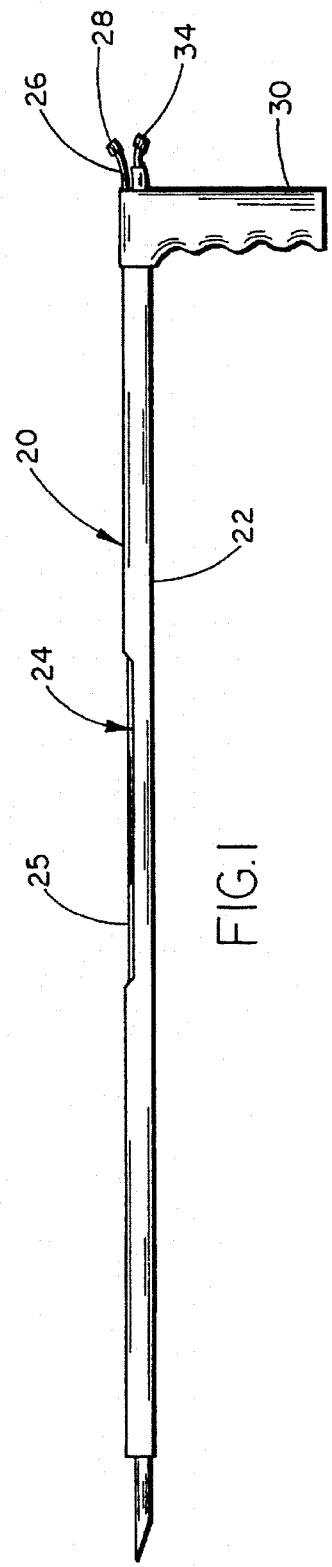
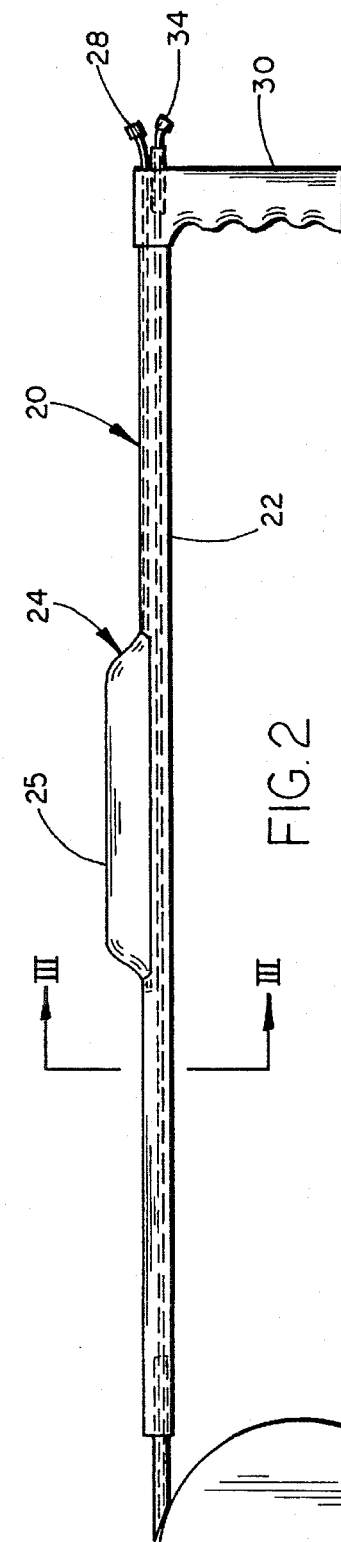
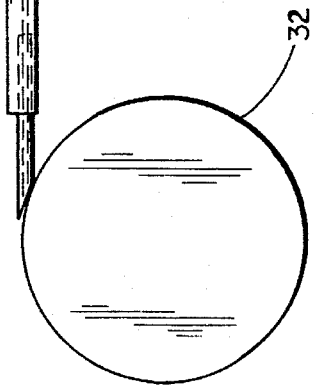

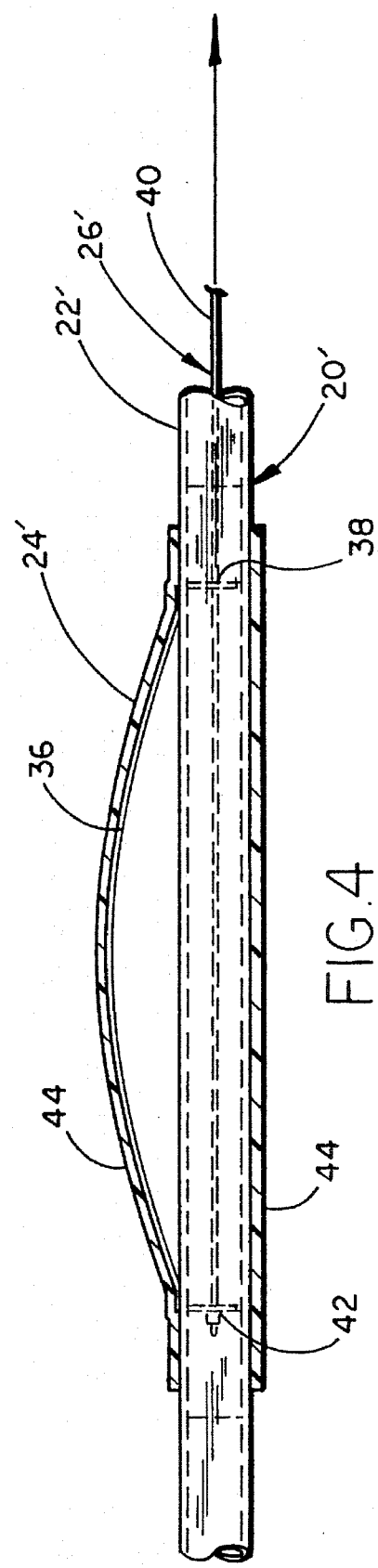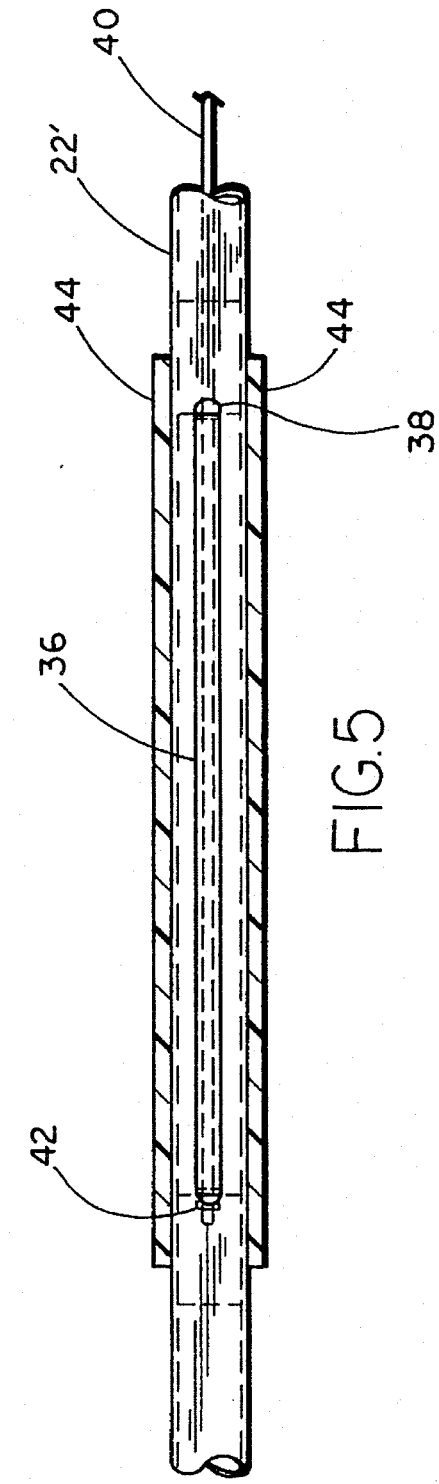

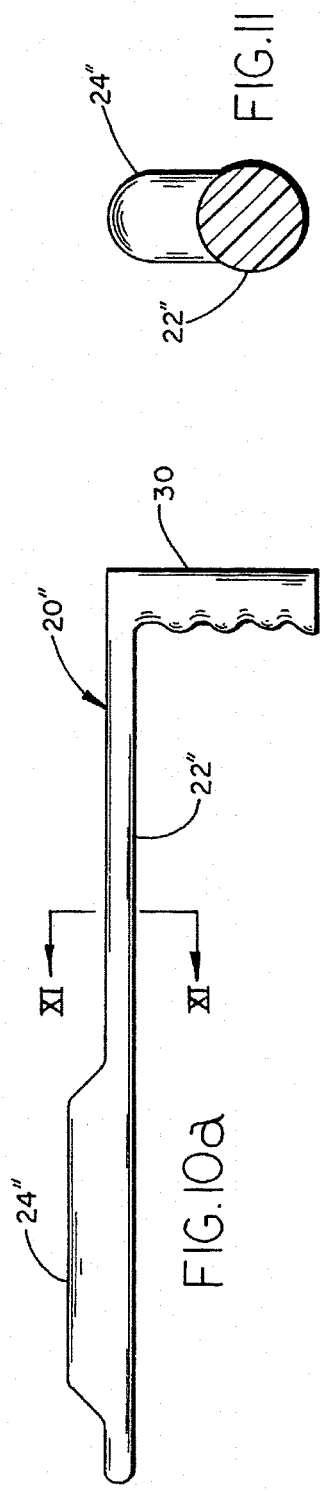
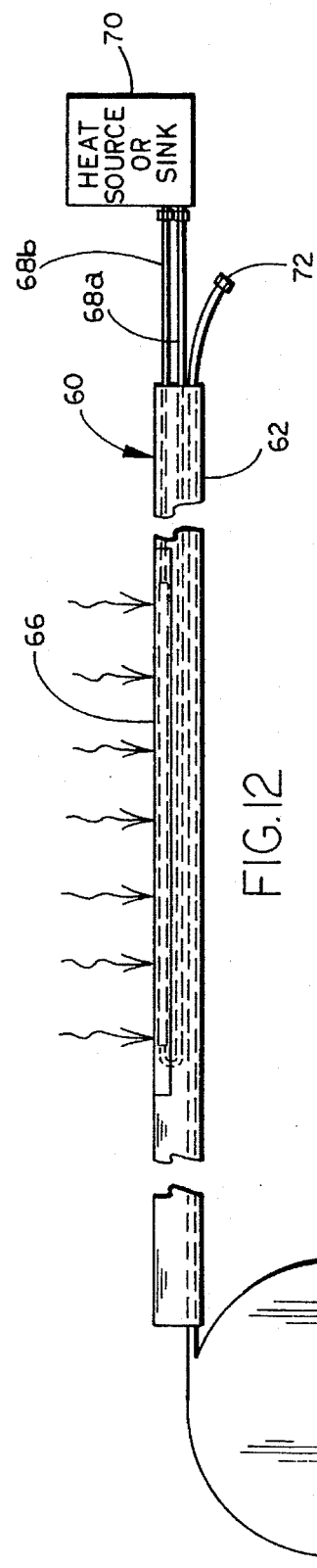
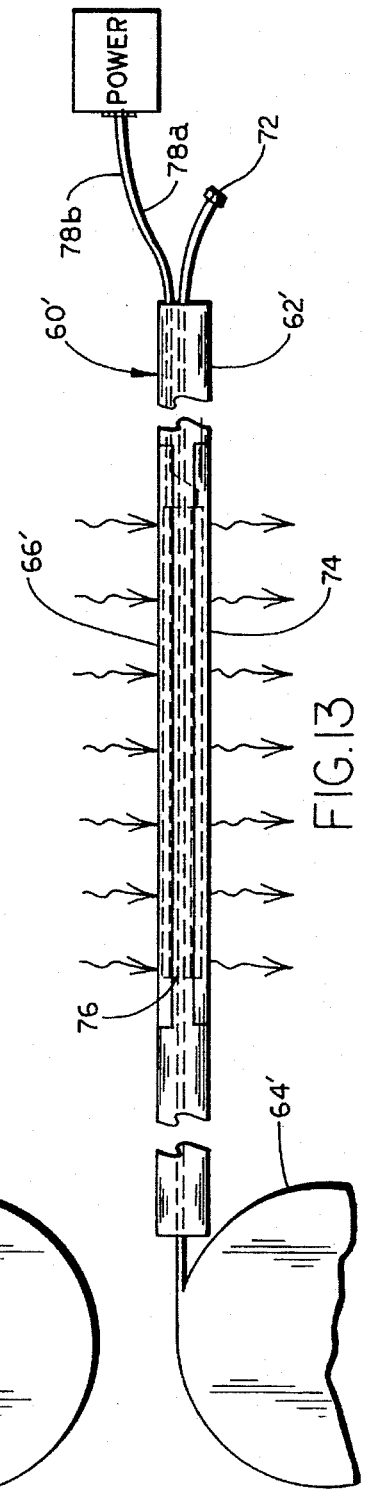

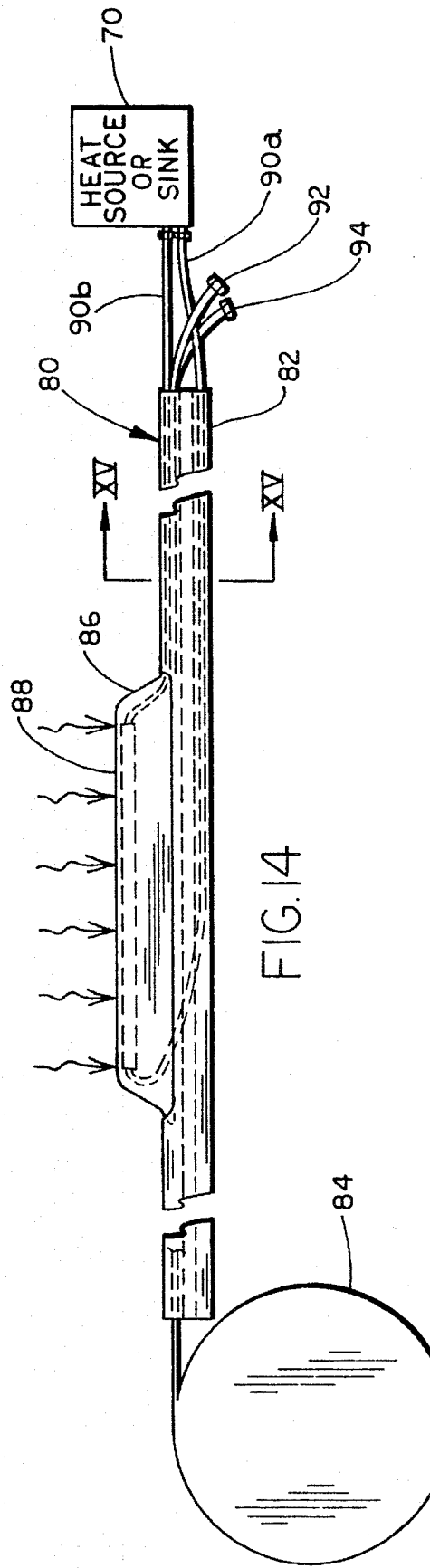
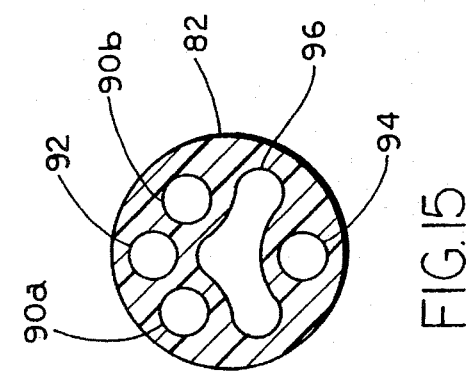
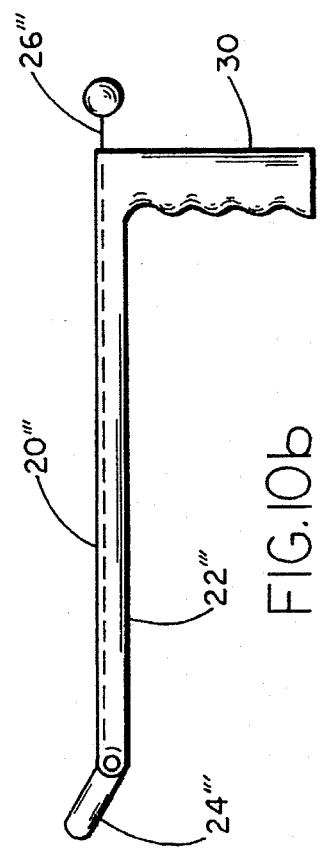

NON-INVASIVE AORTIC IMPINGEMENT AND CORE AND CEREBRAL TEMPERATURE MANIPULATION METHOD

CROSS-REFERENCE TO RELATED APPLICATION

This application is a continuation-in-part of application Ser. No. 08/126,542, filed Sep. 24, 1993, by the present inventors and entitled a MECHANICAL ADJUNCT TO CARDIOPULMONARY RESUSCITATION (CPR), AND AN ELECTRICAL ADJUNCT TO DEFIBRILLATION COUNTERSHOCK, CARDIAC PACING, AND CARDIAC MONITORING.

BACKGROUND OF THE INVENTION

This invention relates generally to medical intervention and, more particularly, to the treating of cardiac arrest patients, patients in various forms of shock, patients suffering hypothermia and hyperthermia, and patients with head injury. More particularly, this invention relates to a method and apparatus for a non-invasive alteration of arterial blood pressures, myocardial and cerebral perfusion pressures, blood flow, cardiac output, and cerebral and core temperatures.

Approximately one million people per year have cardiac arrests in the United States. Less than 10% of these people are discharged from the hospital alive without neurological damage. This percentage of people discharged would be increased if the treatment available after the onset of cardiac arrest was improved. Areas in which this treatment could be improved include: (1) artificial circulation during cardiopulmonary resuscitation (CPR); (2) induction and maintenance of a state of therapeutic hypothermia; (3) induction and maintenance of brief periods of cerebral hypertension after return of spontaneous circulation; and (4) continued circulatory support for the brain and heart after return of spontaneous circulation from cardiac arrest.

The blood of a cardiac arrest patient is artificially circulated during CPR by cyclically compressing the chest. One major theory describing how artificial circulation is generated during CPR states that compression of the chest causes global increases in intrathoracic pressure. This increase in intrathoracic pressure in the thoracic compartment is evenly distributed throughout the lungs, the four chambers of the heart as well as the great vessels in the chest. The increase in thoracic pressure is greater than in the compartments above and below the chest. These compartments mainly include the neck and head above the chest and the abdominal compartment below the diaphragm and chest. When thoracic pressure is increased above the pressure in these compartments, blood within the thoracic cavity moves to the head and abdomen with greater blood flow going toward the head. When the chest is released, the pressure within the thoracic cavity drops and becomes less than the pressure within the head and abdomen, therefore allowing blood to return to the thoracic cavity from the head and abdominal compartments. This theory of CPR-produced blood flow is termed the "thoracic pump mechanism," whereby the entire thorax itself acts as a pump with the heart itself acting as a passive conduit for blood flow. This theory is different from the cardiac pump mechanism, which states that compression of the chest produces blood flow by compressing the heart between the sternum and anterior structures of the vertebral column. In most patients, blood flow produced during chest compressions is likely a combination of the two theories. In each individual patient, blood flow during CPR depends on various factors such as body habitus, with thinner individuals relying more on the cardiac pump mechanism of blood flow, and in larger individuals with increased anterior-posterior chest dimension relying on the thoracic pump mechanism. Both mechanisms of blood flow have been shown to be present in animal and human studies. Regardless of which mechanism is invoked, currently performed standard chest compressions as recommended by the American Heart Association produces 30% or less of the normal cardiac output. This results in extremely poor regional cerebral and myocardial blood flow during CPR. The level of blood flow generated during CPR is usually insufficient to re-start the heart and prevent neurologic damage. The purpose of CPR is to attempt to sustain the viability of the heart and brain until more definitive measures, such as electrical countershock and pharmacotherapy, are administered to the patient.

A main determinant for successful resuscitation from cardiac arrest is the coronary perfusion pressure produced during CPR. Coronary perfusion pressure (CPP) is defined as the aortic diastolic pressure minus the right atrial diastolic pressure. CPP represents the driving force across the myocardial tissue bed. Animal studies are plentiful which demonstrate that CPP is directly related to myocardial blood flow. It appears in humans that a CPP of at least 15 mm Hg is required for successful resuscitation. CPP of this magnitude is difficult to achieve with chest compressions alone. Patients, who utilize the thoracic pump mechanism for CPR, are even more unlikely to be able to produce this level of CPP during CPR alone. The major means for producing coronary perfusion pressures high enough for successful resuscitation have been to perform more forceful chest compressions and by administering various adrenergic agonists, such as epinephrine. Unfortunately, it has been shown that CPPs are difficult to augment with chest compressions alone and that in some situations very high doses of adrenergic agonists are required to produce higher CPPs. The difficulty in trying to produce higher CPPs with CPR alone lies in the fact that right atrial diastolic pressures are sometimes increased to the same or greater magnitude as aortic diastolic pressures. Using various adrenergic agonists, aortic diastolic pressure is usually augmented to a higher degree than right atrial diastolic pressure. However, the use of adrenergic agonists to achieve this have several drawbacks. These include increasing myocardial oxygen demands to a greater degree than can be met with blood flow produced during CPR. In addition, there are lingering effects of adrenergic agonists which may be detrimental after successful return of spontaneous circulation. These include periods of prolonged hypertension and tachycardia, which may further damage the heart and possibly cause re-arrest.

Cerebral perfusion pressure is a main determinant of cerebral blood flow. During cardiac arrest and CPR, autoregulation of blood flow in the brain may be lost. Cerebral perfusion pressure is defined as the mean arterial pressure minus the intracranial pressure. The main determinant of mean arterial pressure during CPR is aortic diastolic pressure. One of the main determinants of intracranial pressure during CPR is the mean venous pressure in the central circulation and the neck. Forward flow to the head is produced during CPR because of functional valves at the neck veins entering the thorax. These valves close during chest compressions, which prevent venous pressure transmission and flow of blood back into the neck and cranium. When these valves are not functioning, pressure is transmitted during the chest compression to the neck veins and into the cranium. This in effect decreases forward cerebral blood flow. Methods that increase cerebral blood flow during conventional CPR are mainly the use of adrenergic agonists. These agents selectively increase arterial pressure over venous pressure. Thus, mean arterial pressure becomes greater than intracranial and cerebral venous pressure thus producing net forward flow. However, use of adrenergic agonists have several drawbacks. In conventional doses, increases in cerebral blood flow are extremely variable with many individuals having no response at all. The use of higher doses of adrenergic agonists may be problematic as previously discussed under myocardial blood flow.

In summary, the major deficiencies in CPR-produced blood flow to the critical organs of the heart and brain are primarily due to the inability of conventionally performed CPR to cause highly selective increases in aortic diastolic pressure without causing increases of similar magnitude in central venous pressures. The ability to maximize the former while minimizing the latter would be extremely advantageous especially if the effects could be immediately reversed.

Several techniques have been developed to take advantage of the various CPR-produced mechanisms of blood flow. Two techniques that take advantage of the thoracic pump mechanism include simultaneous ventilation compression CPR (SVC-CPR) and vest-CPR. SVC-CPR is a technique that involves inflating the lungs simultaneously during the chest compression phase of CPR. This causes larger increases in intrathoracic pressure than external chest compression alone without ventilation or without external chest compression. This has been shown in animal studies to result in higher cerebral blood flows than in conventionally performed CPR. However, one major drawback is that coronary perfusion pressures are not uniformly increased and, in some instances, can be detrimentally decreased. When SVC-CPR was tested in a clinical trial, no increases in survival were noted over standard CPR.

Vest-CPR is a technique which utilizes a bladder containing vest analogous to a large blood pressure cuff and is driven by a pneumatic system. The vest is placed around the thorax of the patient. The pneumatic system forces compressed air into and out of the vest. When the vest is inflated, a relatively uniform decrease in circumferential dimensions of the thorax is produced which creates an increase in intrathoracic pressure. Clinically, the vest apparatus is cyclically inflated 60 times per minute with 100 mm Hg-250 mm Hg pressure which is maintained for 30%-50% of each cycle with the other portion of the cycle deflating the vest to 10 mm Hg. Positive pressure ventilation is performed independent of the apparatus after every fifth cycle. When studied clinically in humans, and compared with manually performed standard external CPR, the vest apparatus produced significantly higher coronary perfusion pressures and significantly higher mean aortic, peak aortic, and mean diastolic pressures. However, these changes are not uniformly seen in all patients. Of note, when the vest has been studied in the laboratory and clinical settings, larger doses of epinephrine have been used to achieve these higher coronary perfusion pressures since the thoracic pump model would predict aortic diastolic and right atrial diastolic pressures to be equivalent during the relaxation phase (when coronary perfusion occurs).

Another new technique, which takes some advantage of both the thoracic and cardiac pump mechanism of blood flow, is called "active compression/decompression CPR (ACDC-CPR)." This technique utilizes a plunger-type device, which is placed on the patient's sternum during cardiac arrest. The person performing chest compressions presses on the device which causes downward excursion of the anterior chest wall. The person then pulls up on the device. Since the device is attached to the sternum by suction, this causes the anterior chest to be actively recoiled instead of undergoing the usually passive recoil of standard external CPR. This active recoil is capable, in many individuals, of causing a decrease in intrathoracic pressure, which is transmitted to the right atrium thus lowering right atrial pressure during artificial diastole and, in turn, increasing coronary perfusion pressure. This negative right atrial pressure also has the effect of increasing venous return to the thoracic cavity, which may enhance cardiac output. Factors, such as body habitus and chest wall compliance, which impact on the efficacy of ACDC-CPR have not been studied, but are likely to have an effect. Persons with larger body habitus probably would receive less benefit from the technique.

Two other techniques, which are being investigated to resuscitate victims of cardiac arrest, and which do not rely on a mechanism of CPR-produced blood flow, include selective aortic arch perfusion and cardiopulmonary bypass. Both of these techniques require access to the central arterial vasculature. Selective aortic perfusion is experimental and involves percutaneously placing a balloon catheter in the aortic arch through a vessel, such as the femoral artery. The balloon catheter is placed in the aortic arch and the inflated balloon positioned just distal to the take-off of the carotid arteries. Perfusion takes place under pressure with oxygenated fluids or blood for various lengths of time. In this manner, the brain and heart are selectively perfused with little or no perfusion taking place distal to the occluded portion of the aorta. Over time, the central venous pressures will rise. This technique has not been tested clinically, but is expected to take a high level of expertise and cannot be readily performed in a setting outside of the hospital where many cardiac arrests occur.

Cardiopulmonary bypass during CPR is performed by obtaining central arterial and venous access usually percutaneously through the femoral artery and vein. This technique is capable of totally supporting the circulation by producing near normal cardiac outputs and blood flows to the heart and brain. Although shown to be effective, there are many technical difficulties which make its widespread use unfeasible. Large cannulas must be placed in the femoral artery and vein, which is difficult in the collapsed circulation. The bypass circuit is complicated and, if not properly primed, may produce air emboli. In addition, the patient requires systemic anticoagulation in most instances. The use of such a technique during CPR can be performed only at specially equipped centers with specially trained personnel.

Open-chest CPR is an old technique that was commonly performed before the advent of modern-day CPR. This technique involves opening the patient's chest by performing a thoracotomy. The descending aorta is usually cross-clamped. The heart itself is then manually massaged (compressed) with the hands. Although this technique is effective in producing heart and brain blood flows superior to standard CPR, it does not lend itself to widespread performance especially in the out-of-hospital setting. Reasons for this include the level of expertise required and the hazard of blood-borne pathogens. Other special equipment, such as the Anstadt cup, can be directly placed on the heart to mechanically compress the heart but, of course, have the same disadvantage of requiring a thoracotomy.

Two post-resuscitative interventions found to improve neurologic outcome in animal models of cardiac arrest is a brief period of immediate post-resuscitation hypertension and rapid induction and maintenance of cerebral hypothermia. The mechanisms for improved neurologic outcome with post-resuscitation hypertension is unclear. It is thought that this brief period of hypertension clears cerebral vessels of microthrombi, which may clog the cerebral circulation following cardiac arrest. It is also thought that this brief period of hypertension may help to prevent some of the post-resuscitation cerebral low flow and "no flow phenomenon," which contributes to neurologic injury. Post-resuscitation hypertension may decrease the overall amount of cerebral damage caused by cardiac arrest. One difficulty in providing for post-resuscitation hypertension is that the common means of producing this, through the use of adrenergic agonists, also produces considerable metabolic demands on the cardiovascular system.

Although shown to be very effective, production and maintenance of post-resuscitation hypothermia is extremely difficult to rapidly produce within a time frame immediately after restoration of spontaneous circulation following cardiac arrest. Although a decrease in cerebral temperature from 37° C. to 34° C. has proven to be neuroprotective, even a small drop of 3° is difficult to rapidly produce. In order to be effective, this mild degree of hypothermia must be produced within several minutes of the resuscitation. Methods, such as isolated head cooling by placement of the head in an ice bath, nasopharyngeal cooling, injection of the carotid circulation with cooled solution, thoracic and peritoneal lavage, and placement of the head and thorax in a cooling helmet and jacket are all problematic in that hypothermia is not attained rapidly enough or if attained cannot be maintained for a sufficient duration of time to be neuroprotective. Although cardiopulmonary bypass can produce a state of therapeutic hypothermia very rapidly, its institution either with traditional placement through a median sternotomy or through peripheral placement percutaneously via the femoral artery and femoral vein is too time-consuming for it to be of practical use in the emergency setting. Thoracic and peritoneal lavage, although effective, are also somewhat time-consuming and cumbersome in the emergency setting especially when ongoing resuscitative efforts are required. Carotid flush is effective but would involve needle or catheter placement into the internal carotid artery, which may be impractical, difficult to achieve, or unsafe. Although almost immediate brain cooling can be achieved with carotid flushing, once restoration of spontaneous circulation is achieved, continuous infusion would be required to maintain cerebral hypothermia. Cooling jackets and cooling helmets, along with placement of the head in an ice bath, require too long of a time period to be effective in rapidly reducing cerebral temperature. The main problem with these techniques is that if cooling is not simultaneously accompanied by sufficient blood flow, rapid temperature drops are unlikely to occur. This is especially true of external cooling because the amount of blood flow and temperature gradient required to cause rapid drops in core temperature are quite large. The same problems exist when attempting to rapidly induce hypothermia in victims of head trauma.

Cardiogenic shock has many causes, including myocardial infarction, various forms of myocarditis, and other causes of myocardial injury. When severe, this condition becomes self-perpetuating secondary to the inability of the host to provide for adequate myocardial blood flow. This may result in further myocardial dysfunction leading to inadequate cerebral and myocardial blood flow and eventually to cardiac arrest. Cardiogenic shock may also be first noted after resuscitation from cardiac arrest depending on the length of the cardiac arrest. Cardiogenic shock may sometimes be difficult to distinguish from other forms of shock. Survival might be enhanced if myocardial and cerebral perfusion could be maintained until other definitive diagnostic and therapeutic measures could take place.

Immediate survival from cardiogenic shock will depend on maintenance of myocardial and cerebral blood flow. Various forms of treatment are available for cardiogenic shock, including various forms of pharmacotherapy and intra-aortic balloon pumping. Pharmacotherapy, while effective, requires invasive hemodynamic monitoring, such as pulmonary artery catheter placement for optimal titration. This may be difficult to institute in a timely manner when severe cardiogenic shock is first encountered especially in the pre-hospital setting. Intra-aortic balloon pumping in which a balloon catheter is placed into the thoracic aorta is effective but somewhat complicated to perform. Special equipment is needed for its placement and can only be performed at facilities which are capable of placing and maintaining such equipment and patients. Intra-aortic balloon pumping increases cardiac output by decreasing cardiac afterload. A balloon inflates during the diastolic portion of a cardiac cycle. This reduces cardiac afterload, thus lessening the workload on the heart. This balloon inflation during diastole also forces blood cephalad, thus perfusing the myocardial and cerebral tissues more effectively.

Other forms of shock, such as septic and neurogenic shock, cause hypoperfusion of critical organs due to a relative hypovolemia. Vascular tone is lost and requires a combination of volume replacement and vasopressors to maintain critical perfusion to vital organs. Immediate effective therapy aimed at maintaining cerebral and myocardial perfusion is difficult to institute because the various forms of shock are at times difficult to differentiate and therapy may differ between types of shock, although the immediate goal is to preserve myocardial and cerebral perfusion.

The major underlying immediate cause of death from any shock state is inadequate myocardial and cerebral perfusion. Survival with intact neurologic function is likely to be enhanced if myocardial and cerebral blood flow can be maintained until the underlying cause of the shock state can be optimally diagnosed and treated.

Head injury can be devastating. Much of the neurologic damage that takes place occurs after the initial insult. Therapeutic measures, which have been shown to aid victims of head trauma, include induction of therapeutic hypothermia and maintenance of cerebral blood flow in the face of increased intracranial pressure. These measures have been difficult to institute within the first several hours after the initial injury especially if other extra-cerebral organs are simultaneously injured. Outcome might be improved in victims of head trauma if maintenance of cerebral blood flow with induction of mild hypothermia could take place as soon after the initial injury as possible.

Hypothermia has been shown to improve the survival and reduce the amount of injured neurologic tissue. Several proposed mechanisms by which this happens are decreases in the metabolic requirements of the injured tissue, as well as decreases in the secretion of damaging neurotransmitters by the injured tissue. Production of hypothermia in head-injured patients has been limited to cooling blankets, which produce whole body cooling. Although sometimes effective, whole body cooling is difficult to initiate early especially in cases where other organ systems have been concomitantly traumatized in the initial injury. Blood flow to injured brain tissue is many times reduced below critical levels required to maintain survival when intracranial pressure is increased. Cerebral blood flow may be extremely difficult to maintain after the initial injury especially when multiple organ systems are involved in the trauma. Mean arterial blood pressure can also be difficult to maintain because of the ongoing blood loss into the thoracic and abdominal cavities or from extremity injuries. Intracranial pressure increases because of brain edema from the cerebral injury, or from expanding pools of blood from torn vessels in the brain or skull itself. Currently, the main mechanisms for reducing intracranial pressure involve the administration of diuretics, such as furosemide and mannitol, administration of steroids which reduce cerebral edema over time, removal of cerebral spinal fluid, elevation of the head which promotes venous drainage, administration of barbiturates which reduce the metabolic demand of brain tissue, hyperventilation producing hypocapnia and reduced cerebral blood flow which decreases intracranial pressure, and, as a last resort, removal of less necessary parts of the brain itself. Many of these therapies cannot be performed during the initial care of the multiply injured trauma patient who has both neurologic injury and multiple organ system injury, or have significant side effects. Administration of diuretics produce further volume depletion and may further reduce mean arterial pressure. Steroids require several hours to begin taking effect. Removal of cerebral spinal fluid and damaged brain tissue itself may take several hours to perform. Administration of barbiturates may also reduce the mean arterial pressure. Hyperventilation, although effective in reducing intracranial pressure, does so by decreasing cerebral blood flow which may be injurious to damaged tissue. All of these therapies become more complicated in the presence of other extra-cerebral organ injury. Occasionally, pharmacotherapy to raise mean arterial blood pressure is used to help maintain cerebral perfusion pressure in the face of rising intracranial pressure. This is difficult and sometimes dangerous to institute early because vasopressors many times increase the metabolic demands of other injured tissues.

Prolonged exposure to cold or hot environments under certain conditions can result in life threatening states of hypo- or hyperthermia, respectively. Patients may be present with various forms of shock or various forms of altered mental status. Survival may be enhanced if rapid normalization of body temperature (especially that of the heart and brain) takes place while maintaining adequate perfusion to the heart and brain. In cases of hypothermia, an attempt is made to raise core body temperature as rapidly as possible to near normal levels. Life threatening dysrhythmias and dysfunction of the heart may simultaneously occur from hypothermia, which makes ongoing rewarming efforts more difficult to carry out. Methods of rewarming have included passive rewarming with blankets and heating lamps, and active rewarming with cardiopulmonary bypass, infusion of warmed intravenous fluids, peritoneal, bladder, gastric, thoracic, and mediastinal lavage, and breathing of warm humidified air. Many of these methods are ineffective and are capable of only raising core temperature at a rate of 1° C. per hour. Some will be rendered totally ineffective based on the victim's circulatory status. Others, such as peritoneal and thoracic lavage with warm fluid, are effective but are time-consuming and difficult to control. In addition, they cannot help support the circulation during shock. Cardiopulmonary bypass is effective, but is time-consuming and requires an extensive level of expertise. Most of these methods cannot be performed outside of the hospital.

Treatment of hyperthermic emergencies requires the ability to rapidly lower the body's core temperature to normal in order to avoid shock, cardiac arrest, and various forms of neurologic damage. Treatments currently used include ice packing, lavage of various body cavities with cooled fluids, and convection with water spray and fanning. Some of the methods will be totally ineffective based on the status of the patient's circulation. In addition, if countershock or electrical cardiac pacing is required, safety hazards are present because the surface of the body is wet depending on the cooling technique used. In addition, none of the above methods will be capable of simultaneously supporting the circulation. Of course, the critical organs requiring support will be the heart and brain.

Hemorrhagic shock is a leading cause of death from trauma. Many times there are delays in reaching hospitals which are qualified to take care of the complex injuries of such individuals. Many patients who die of trauma, die from multi-system involvement. Multi-system involvement may include head injury along with injuries to organs of the thoracic and abdominal cavity. Uncontrolled hemorrhage leading to hypovolemic shock is a leading cause of death from trauma especially from blunt and penetrating trauma of the abdomen. When head trauma occurs concomitantly with thoracic and abdominal hemorrhage, the brain becomes hypoperfused and, thus, becomes at greater risk for secondary injury. Currently, in the pre-hospital and emergency department setting, there are limited means to control exsanguinating hemorrhage below the diaphragm while maintaining myocardial and cerebral blood flow. Definitive control of hemorrhage is performed at surgery but this may be delayed and may not occur within the golden hour (time from injury to definitive treatment/repair) where the best opportunity lies in salvaging the patient. Survival with improved neurologic outcome might be enhanced if means were available to slow or stop ongoing hemorrhage (especially below the diaphragm) while maintaining adequate perfusion to the heart and brain until definitive treatment of the hemorrhage is available. This would be especially true of trauma victims whose transport to appropriate medical facilities would be prolonged.

The use of the pneumatic anti-shock garment (PASG) has met with varying degrees of success depending on the location of injury. This garment is placed on the legs and abdomen and is then inflated. Hemorrhage in the abdominal cavity, as well as the lower extremities, is controlled through tamponade while systemic blood pressure is raised partially through autotransfusion and by raising peripheral vascular resistance. Use of the PASG can sometimes be cumbersome and does not uniformly control hemorrhage or raise blood pressure. In addition, persons with concomitant penetrating thoracic injuries may hemorrhage more when the device is applied. The device may also raise intracranial pressure, which might detrimentally alter cerebral blood flow resulting in neurologic injury.

Other more drastic means to control abdominal bleeding prior to surgery have been the use of thoracotomy to cross-clamp the thoracic aorta and the use of balloon catheters placed into the aorta from the femoral arteries to a point above the celiac-aortic axis. These techniques have met with varying degrees of success and require a high degree of skill and cannot be performed in hospitals not equipped to care for trauma patients or by paramedical care personnel.

Deliberately keeping hemorrhaging trauma victims in a hypotensive state is currently being examined as a means to improve survival. This is done based on the premise that overall hemorrhage (especially abdominal hemorrhage) is reduced if mean arterial pressure is kept low by not aggressively volume-repleting the victim prior to surgery. Unfortunately, this may be dangerous for trauma victims with concomitant head injury or myocardial dysfunction.

An important cause of hemorrhagic shock not caused by trauma includes rupture of abdominal aortic aneurysms. These can occur suddenly and without warning. Control of bleeding even at surgery can be difficult. Temporary measures discussed above for hemorrhage secondary to trauma have been tried for hemorrhage secondary to aneurysm rupture. The same difficulties apply. Survival might be enhanced if hemorrhage could be controlled earlier while maintaining perfusion to the heart and brain.

SUMMARY OF THE INVENTION

The present invention provides a non-invasive method and apparatus for treating cardiac arrest patients, patients in various forms of shock, such as hemorrhagic, cardiogenic, neurogenic and septic, patients suffering hypothermia and hyperthermia, and patients with head injury. The invention relates to a device for inserting into an externally accessible tube of the patient, such as the patient's esophagus, to alter arterial blood pressures, myocardial and cerebral perfusion pressures, blood flow, cardiac output, and body temperatures of the patient.

A non-invasive method of enhancing cerebral and myocardial perfusion in a patient, according to an aspect of the invention, includes positioning a device in a portion of the patient's esophagus juxtaposed with the patient's descending thoracic aorta. The device is used to move, or displace, a wall of the portion of the esophagus posterior-laterally in the direction of the descending thoracic aorta in order to at least partially occlude the descending thoracic aorta. This increases central and intracranial arterial pressure without increasing central and intracranial venous pressure.

A non-invasive method of manipulating core and cerebral temperature of a patient, according to another aspect of the invention, includes positioning in the patient's esophagus a device having a heat transfer surface. The device is positioned in a manner that the heat transfer surface is juxtaposed with a thoracic vessel through which blood is flowing, such as the aortic arch, the carotid arteries, the descending aorta or the heart. Heat is exchanged between the heat transfer surface and blood flowing through the vessel across the wall of the esophagus and the wall of the vessel.

A non-invasive device for at least partially occluding the descending thoracic aorta of a patient and for manipulating core and cerebral temperature of a patient, according to yet another aspect of the invention, includes a tubular elongated member configured to a patient's esophagus and having a selectively moveable portion. A displacement mechanism is included for selectively moving the moveable portion in a manner that will displace a wall of the esophagus that is juxtaposed with the portion of the thoracic aorta of the patient in the direction of the aorta. In this manner, at least partial occlusion of the descending thoracic aorta is effected. The device further includes a heat exchange mechanism for exchanging heat across the esophagus wall with blood flowing through a thoracic vessel. In this manner, the beneficial effects of the various aspects of the invention may be combined to provide a circulatory and temperature adjunct to cardiopulmonary cerebral resuscitation, hemorrhage, shock, head injury, hypothermia, and hyperthermia.

These and other objects, advantages, and features of this invention will become apparent upon review of the following specification in conjunction with the drawings.

BRIEF DESCRIPTION OF THE DRAWINGS

FIG. 1 is a side elevation of a device for at least partially occluding the thoracic aorta of a patient, according to the invention;

FIG. 2 is the same view as FIG. 1 with a moveable portion and an anchor bladder of the device enlarged;

FIG. 3 is a sectional view taken along the lines III—III in FIG. 2;

FIG. 4 is a partial side elevation of an alternative embodiment of a device for at least partially occluding the thoracic aorta of a patient, with portions removed to reveal internal structure;

FIG. 5 is a top plan view of the device in FIG. 4;

FIGS. 10a and 10b are side elevations of additional alternative embodiments of a device for at least partially occluding the thoracic aorta of a patient, according to the invention;

FIG. 11 is a sectional view taken along the lines XI—XI in FIG. 10a;

FIG. 12 is a side elevation of a device for manipulating the core and cerebral temperature of a patient;

FIG. 13 is a side elevation of an alternative embodiment of a device for manipulating the core and cerebral temperature of a patient, according to the invention;

FIG. 14 is a device for at least partially occluding the thoracic aorta of a patient and for manipulating the core and cerebral temperature of the patient, according to the invention;

FIG. 15 is a sectional view taken along the lines XV—XV in FIG. 14;

DESCRIPTION OF THE PREFERRED EMBODIMENT

Figure 6:
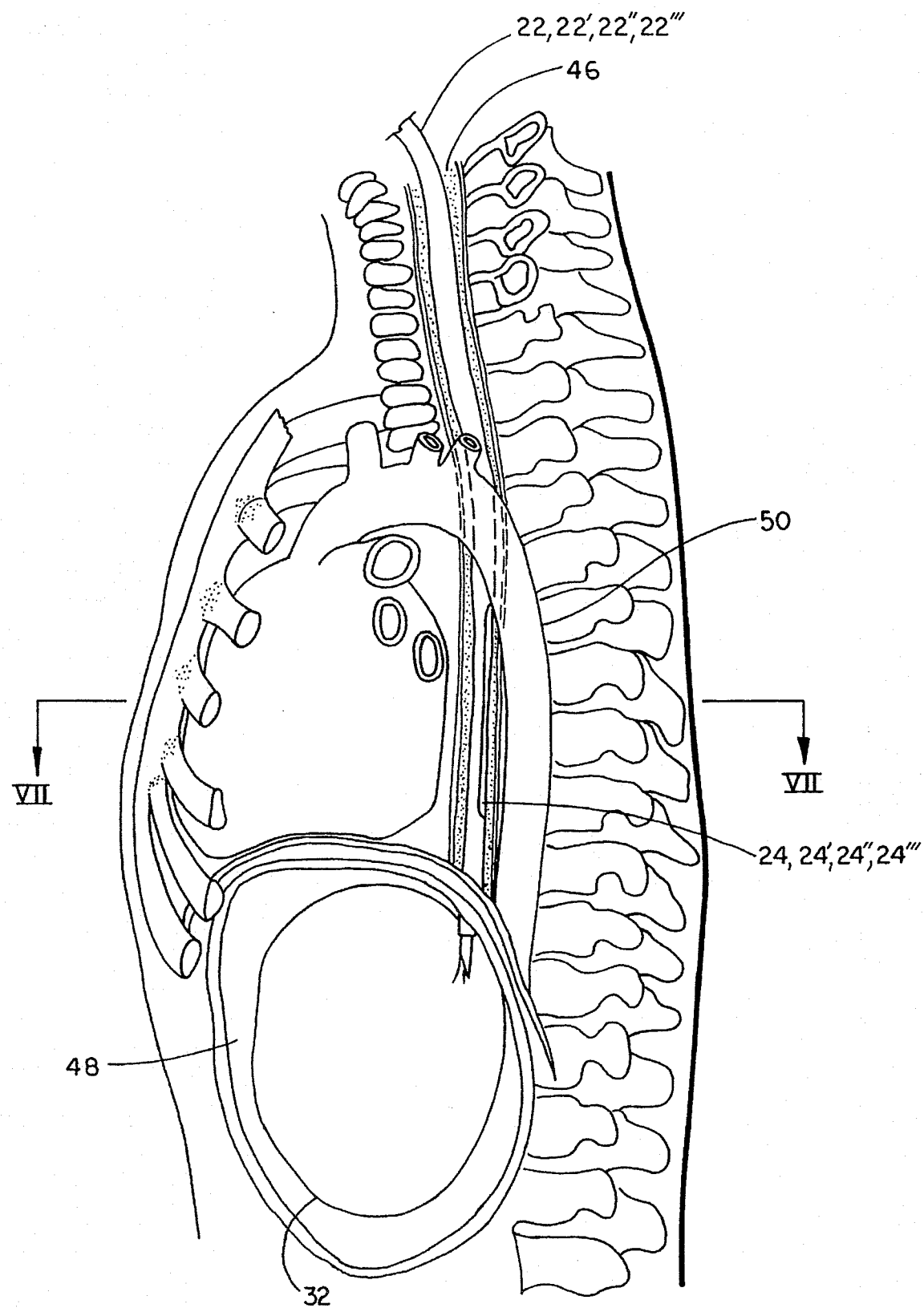
FIG. 6 is a sectional side elevation illustrating a human chest cavity and showing the preferred embodiment of the invention in an operative position.

Referring now specifically to the drawings, and the illustrative embodiments depicted therein, in U.S. patent application Ser. No. 08/126,542, filed by the present inventors on Sep. 24, 1993, for a MECHANICAL ADJUNCT TO CARDIOPULMONARY RESUSCITATION (CPR), AND AN ELECTRICAL ADJUNCT TO DEFIBRILLATION COUNTERSHOCK, CARDIAC PACING, AND CARDIAC MONITORING, the disclosure of which is hereby incorporated by reference, an apparatus is disclosed that includes an esophageal bladder, which when inserted into the esophagus and expanded, hardens the esophagus to provide a platform posterior to the heart against which the heart and aorta are compressed to provide improved artificial circulation during CPR. The compression of the aorta increases aortic pressure, which improves myocardial and cerebral perfusion. In order to further improve myocardial and cerebral perfusion pressure and blood flow, an apparatus 20 is provided for partially or completely occluding a portion of the thoracic aorta of a patient, such as the descending aorta (FIGS. 1–3). Apparatus 20 includes an elongated semi-rigid tubular member 22, which is inserted into the esophagus either nasally or orally. Tubular member 22 includes moveable portion 24, which causes displacement of the esophagus posterior-laterally towards the patient's left side, which allows a long segment of the esophagus to impinge upon an equally long parallel segment of the aorta distal to the aortic arch. Moveable portion 24 is illustrated in FIG. 1 in its non-enlarged state. Apparatus 20 further includes a displacement mechanism 26 for displacing moveable portion 24 in order to displace the esophagus in a manner just described. In the embodiment illustrated in FIGS. 1 and 2, the moveable portion 24 includes a balloon 25, which is expandable by a displacement mechanism 26, which includes connection to a source of pressure (not shown) through an esophageal lumen 28, which extends to balloon 25 in order to enlarge the balloon. Apparatus 20 may additionally include a radial positioning device 30 attached to the portion of tubular member 22 extending outside the patient in order to allow radial adjustment of tube 22 to thereby position moveable portion 24 in a manner that it will move posterior-laterally in the direction of the descending thoracic aorta. In the illustrated embodiment, radial positioning device 30 is illustrated as a handle grip. Apparatus 20 may further include a stomach bladder 32, which is radially offset from member 22 and is enlargeable within the fundus of the stomach in order to anchor member 22 in place. Stomach bladder 32 is enlargeable by a stomach bladder lumen 34, which may be connected with a source of pressure (not shown) in order to inflate bladder 32 after apparatus 20 is positioned in the esophagus. Preferably, esophageal balloon 25 is inelastic so that it may be filled with a liquid or a gas and maintained at a sufficient pressure so that it will be capable of impinging upon the descending thoracic aorta sufficient to substantially completely occlude the descending thoracic aorta. Preferably, esophageal balloon 25 is expanded with an incompressible fluid, such as saline solution.

With apparatus 20 positioned in the patient's esophagus and expandable portion 24 expanded posterior-laterally in the direction of the descending thoracic aorta, cerebral and myocardial perfusion pressures are enhanced in much the same way as by cross-clamping the aorta following thoracotomy. This serves to cause an entirely selective increase in central arterial systolic and diastolic pressure without any concomitant change in central venous and intracranial venous pressures. This, in turn, causes a non-pharmacological rapid increase in coronary and cerebral perfusion pressures and, thus, myocardial and cerebral blood flow.

An alternative apparatus 20' for enhancing cerebral and myocardial perfusion includes a moveable portion 24' having a displacement mechanism 26', which includes a bow 36 made of spring steel and attached at one end 38 within a tubular member 22' (FIGS. 4 and 5). A flexible wire 40 extends through member 22' to the portion of apparatus 20' extending external to the patient (not shown). Wire 40 is attached to a second end 42 of bow 36. In this manner, a tension force placed on wire 40 external to the patient will move the ends 38, 42 of bow 36 close together, resulting in the lateral extension of bow 36 and, hence, displacement of moveable portion 24'. Bow 36 is surrounded by a flexible sheath 44, which isolates the displacement mechanism 26' from the patient and allows expansion of the bow in the direction of the descending thoracic aorta of the patient.

Figure 7:
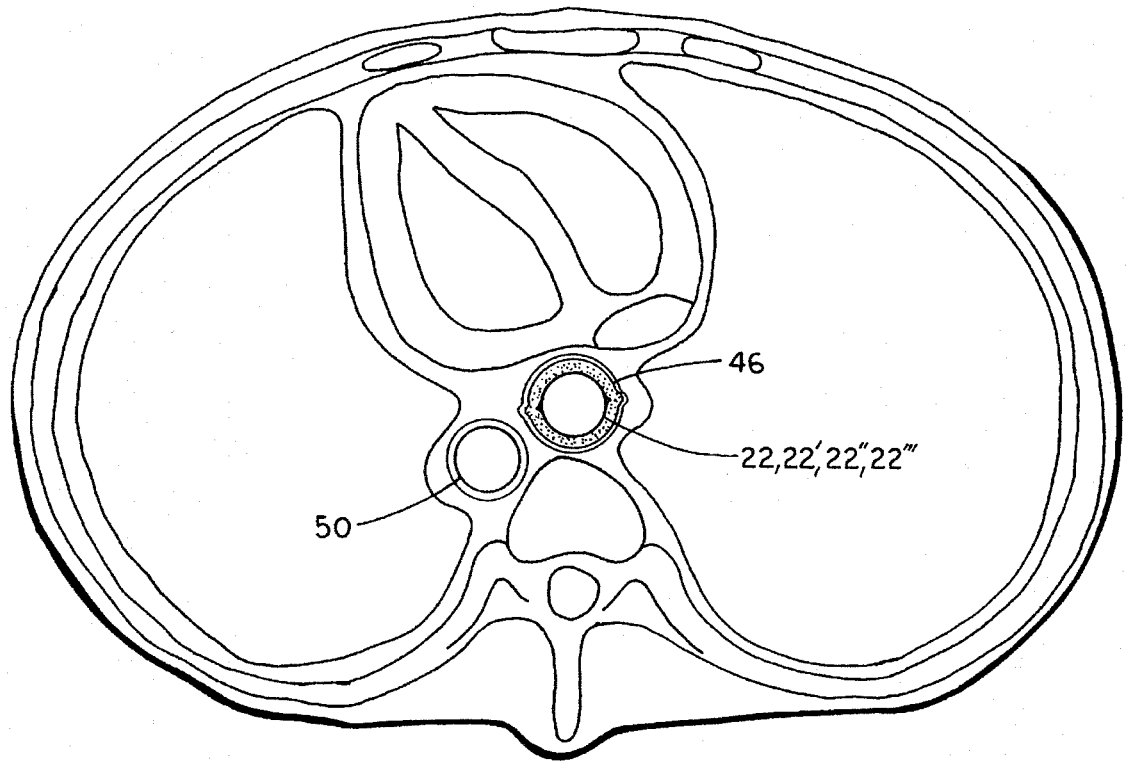
FIG. 7 is a sectional view taken along the lines VII—VII in FIG. 6.
Figure 9:
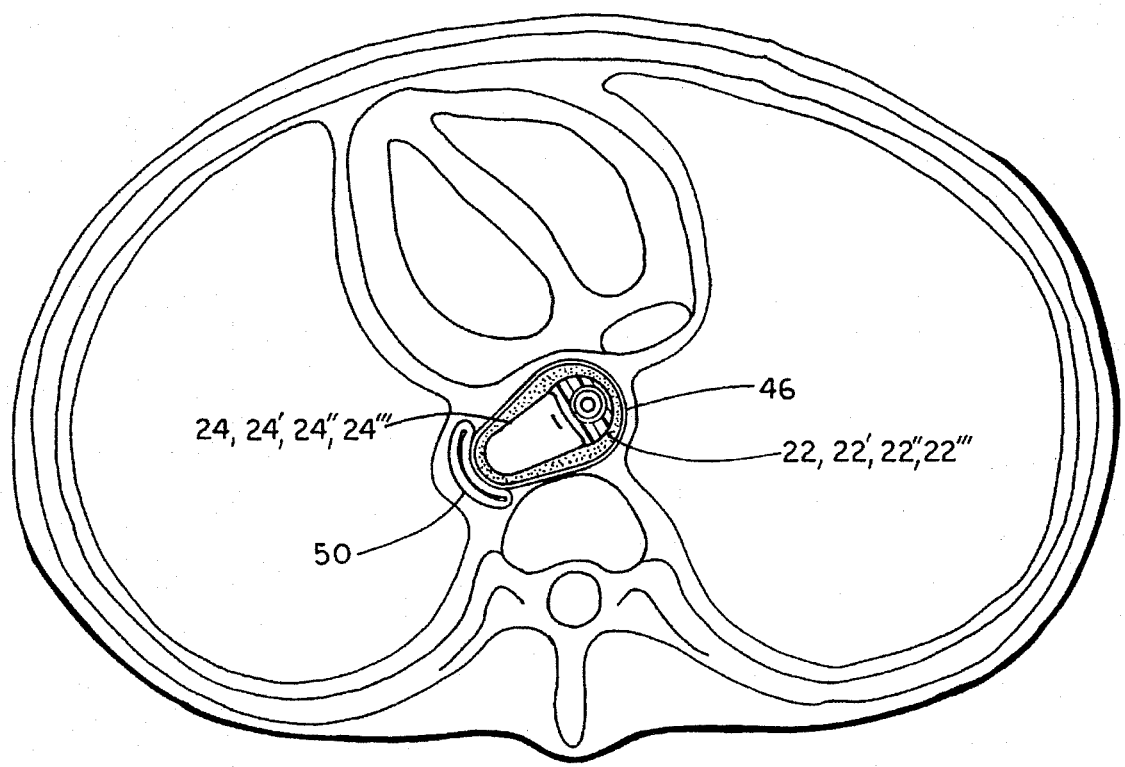
FIG. 9 is a sectional view taken along the lines IX—IX in FIG. 8.
Figure 8:
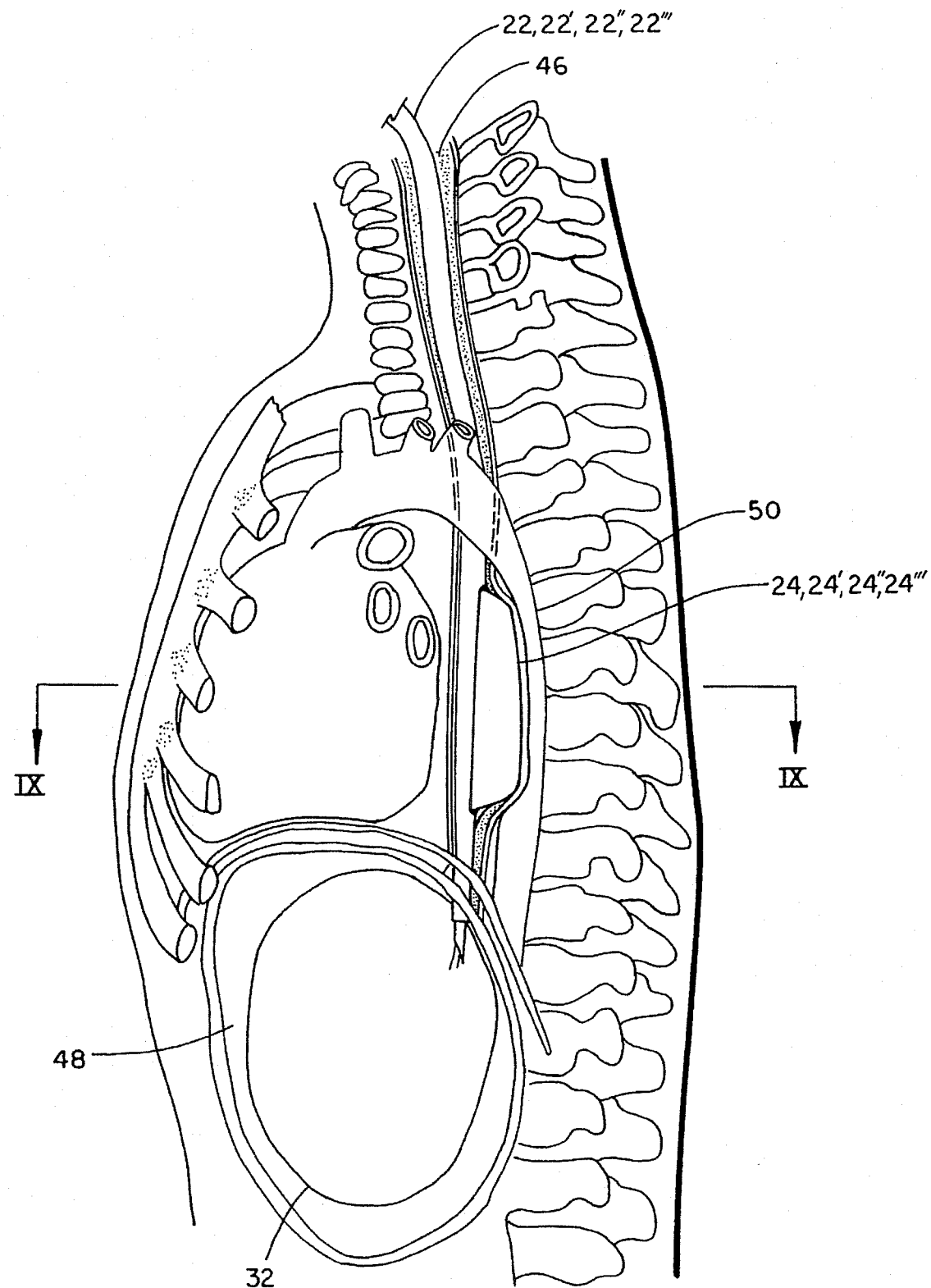
FIG. 8 is the same view as FIG. 6 with the moveable portion of the device enlarged in a manner to displace a wall of the esophagus in the direction of the thoracic aorta.

In use, tubular member 22, 22' of apparatus 20, 20' is inserted in the esophagus 46 of the patient with optional stomach bladder 32 extending into the fundus of the stomach 48 (FIGS. 6–9). As best seen in FIG. 7, member 22, 22' causes the esophagus to become more circular in shape but does not impinge upon the descending aorta 50. Upon actuation of displacement mechanism 26, 26', moveable portion 24, 24' is displaced posterior-laterally in the direction of descending thoracic aorta 50 in order to impinge upon the aorta and partially, or substantially completely, occludes the aorta, as best seen in FIGS. 8 and 9.

Although an apparatus for enhancing cerebral and myocardial perfusion, according to the previously described embodiments of the invention, includes a semi-rigid tube insertable into the patient's esophagus and having an expandable member which may be selectively expanded in the direction of the descending aorta under the operation of a displacement mechanism, the invention may be practiced in other various forms. An apparatus 20" includes a substantially rigid tubular member 22" having a rigid permanently enlarged moveable portion 24" at an end opposite a positioning device 30 (FIGS. 10a and 11). In the illustrated embodiment, apparatus 20" is made of steel. Apparatus 20" may be nasally or orally inserted into the esophagus and radial positioning device 30 manipulated in order to position enlarged portion 24" in the direction of the descending thoracic aorta in order to displace the wall of the esophagus and impinge upon the descending aorta.

An embodiment of a device for enhancing cerebral and myocardial perfusion, which does not require enlargement of the patient's esophagus, is shown in FIG. 10b as an apparatus 20''' having a semi-rigid tubular member 22''' to which is pivotally attached a moveable member 24'''. Moveable member 24''' is pivoted in the direction of the patient's descending thoracic aorta by a displacement mechanism 26''' extending through tubular member 22''' and operable externally of the patient. When apparatus 20''' is properly positioned in the patient's esophagus, the pivotal movement of moveable member 24''' displaces the esophagus wall into impingement with the descending thoracic aorta in order to partially, or completely occlude the aorta, without substantially expanding the esophagus wall.

Indeed, the invention may be carried out without the inclusion of radial positioning device 30 provided that moveable portion 24, 24', 24", 24''' is properly positioned to displace the wall of the esophagus in the direction of the descending thoracic aorta.

In addition to a steady-state, partial or substantially complete, occlusion, the present invention contemplates actuation of displacement mechanism 26, 26', 26''' in synchronism with the ventricular contractions of the patient in order to provide a form of aortic counter-pulse pumping, thus simulating intra-aortic balloon pumping. By reference to FIG. 16, apparatus 20, 20', 20''' is inserted in the patient with displacement mechanism 26, 26', 26''' connected with an intermittent actuator 52. Intermittent actuator 52 is interconnected, as illustrated at 54, with an ECG monitor 56, which monitors the patient's electrocardiogram by way of a pair of electrodes 58a, 58b to externally or internally monitor the patient's electrocardiogram. Actuator 52 actuates the displacement mechanism 26, 26', 26''' in synchronism with ventricular diastole of the patient's cardiogram, as monitored by ECG 56. The counter-pulsation mode, or counter-pulse pump, is most useful in enhancing perfusion pressure upon post-return of spontaneous circulation (ROSC) in order to counteract hypotension upon ROSC. In this manner, myocardial and cerebral blood flow is enhanced in this critical period of ROSC. The counter-pulse pump is also useful in treating other forms of shock with myocardial dysfunction. Alternatively, actuator 52 may be synchronized with a pressure signal from a femoral, or upper extremity, arterial line instead of the signal derived from ECG 56.

Figure 16:
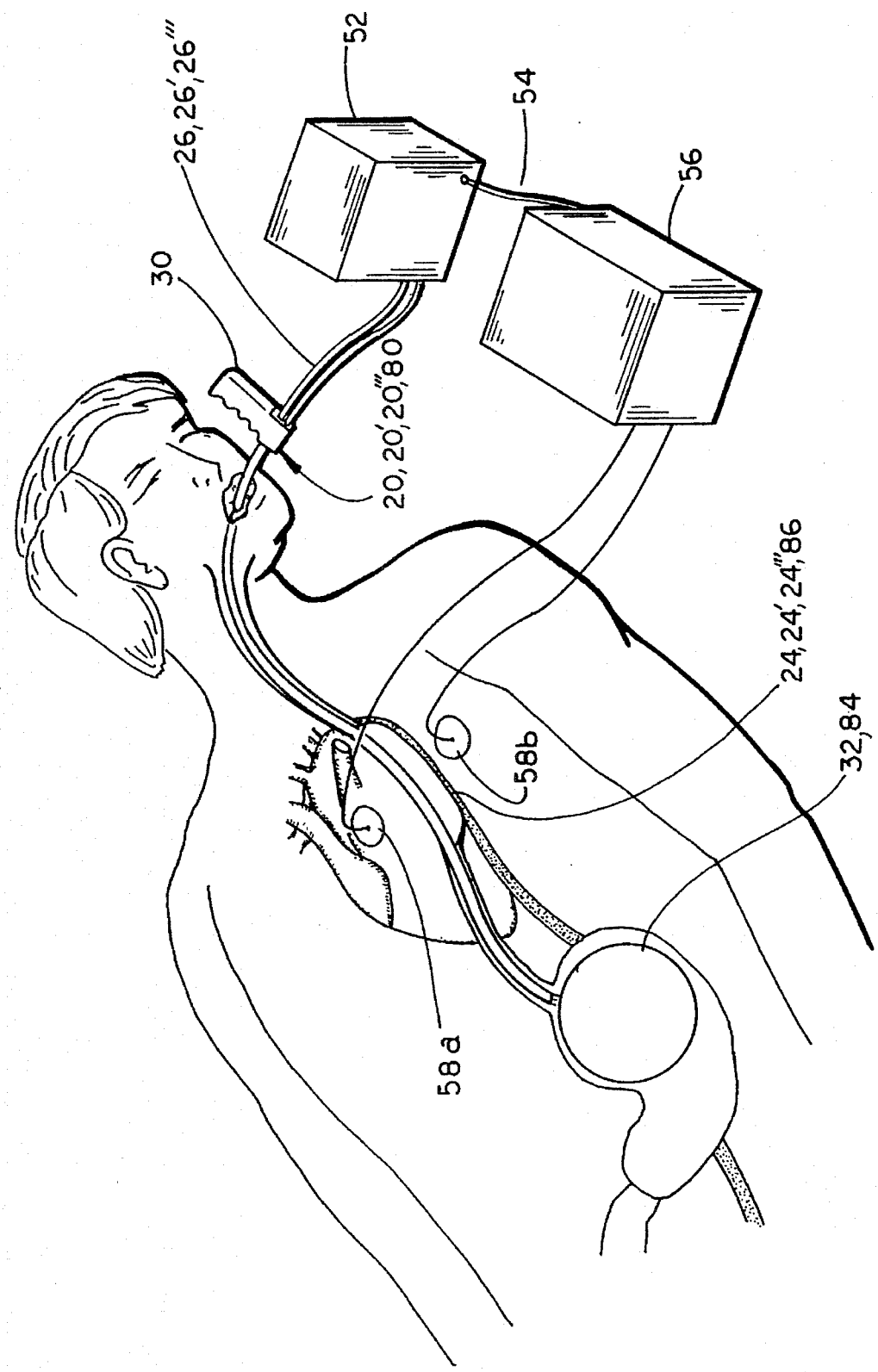
FIG. 16 is a front elevation in section illustrating an apparatus for counter-pulse pumping, according to the invention, in an operable position.

When applying apparatus 20, 20', 20'', 20''' to the patient, the degree of occlusion of descending thoracic aorta 50 may be titrated to blood pressure. This ensures that the apparatus is properly positioned. Such proper positioning is critical for partial occlusion of the descending aorta and counter-pulse pumping, as illustrated in FIG. 16. Blood pressure may be advantageously monitored at the femoral artery, especially if the invention is used to treat shock states. If the apparatus 20, 20', 20'', 20''' is utilized to treat ventricular fibrillation and/or cardiac arrest, then the degree of engagement may be titrated to the metabolic state of the myocardium. The ability to monitor the metabolic state of the myocardium is disclosed in U.S. Pat. No. 5,077,667 issued to Charles G. Brown and Roger Dzwonczyk. If apparatus 20, 20', 20'', 20''' is utilized to provide occlusion for internal bleeding, then proper positioning is achieved when blood pressure stabilizes.

An apparatus 60 is provided, according to the invention, for manipulating core and cerebral temperature of a patient (FIG. 12). Apparatus 60 includes a semi-rigid tubular member 62 for insertion in the patient's esophagus and an optional stomach bladder 64 for anchoring member 62 in the esophagus. Apparatus 60 further includes a heat transfer surface 66, which is positioned against the wall of the esophagus in the direction of a thoracic vessel through which blood flows, such as the descending aorta. Heat transfer surface 66 extends substantially the length of the interface between the esophagus and the descending aorta. Because there are less intervening tissues, such as skin, fat, cartilage, or bone, which may impede temperature change, heat may be transferred more efficiently between the blood flowing through the descending aorta and heat transfer surface 66. Heat is supplied to or removed from heat transfer surface 66 by a fluid circulated through tubes 68a, 68b, which extend between heat transfer surface 66 and a heat source or heat sink 70. A stomach balloon lumen 72 provides for the selective inflation of a stomach bladder 64.

In operation, with apparatus 60 inserted in the esophagus of the patient such that heat transfer surface 66 is against the wall of the esophagus in the direction of the vessel, heat is either supplied to heat transfer surface 66 or withdrawn from heat transfer 66 by fluid flowing through tubes 68a, 68b. The heat is, in turn, either removed from the fluid or added to the fluid by heat source or sink 70. If it is desired to create hypothermia, heat source or sink 70 removes heat from the fluid circulating through tubes 68a, 68b, which, in turn, cools heat transfer surface 66 which draws heat from the blood flowing through the vessel and cools the blood. This, in turn, lowers the core and cerebral temperature of the patient. If it is desired to produce normothermia, heat is added to fluids flowing through tubes 68a, 68b from heat source or sink 70 which raises the temperature of heat transfer surface 66 above the temperature of the blood flowing through the vessel. This raises the temperature of the blood flowing through the vessel and, in turn, raises the core and cerebral temperature of the patient.

An alternative apparatus 60' for manipulating core and cerebral temperature of a patient includes a heat transfer surface 66' positioned with respect to a tubular member 62' in order to abut the wall of the esophagus in the direction of a thoracic vessel through which blood flows, such as the descending aorta. Apparatus 60' includes a second heat transfer surface 74 positioned on member 62' in order to abut a wall of the esophagus in a direction away from the vessel. Apparatus 60' further includes an electrically operated heat pump, such as a thermoelectric device 76, which is capable of transferring heat between heat transfer surfaces 66' and 74. Such thermoelectric devices are well known in the art, are commercially available, and operate under the Peltier principle. Apparatus 60' includes a pair of electrical leads 78a, 78b for connection of device 76 with an electrical source (not shown) in order to supply electrical energy to device 76. Depending upon the polarity of the power supply, thermoelectric device 76 either removes heat from heat transfer surface 66' and discharges the removed heat to heat transfer surface 74, or vice versa. The heat removed from the blood flowing through the thoracic vessel is discharged to the tissue surrounding the portion of the esophagus in contact with heat transfer surface 74. Likewise, heat added to the blood flowing through the thoracic vessel through transfer surface 66' is drawn from the tissue surrounding the portion of the esophagus contacted by heat transfer surface 74.

An apparatus 80 is capable of at least partially occluding the descending aorta of the patient, as well as manipulating the core and cerebral temperature of a portion of a patient (FIGS. 14 and 15). Apparatus 80 includes a semi-rigid tubular member 82, which is configured for positioning in the esophagus of a patient. Apparatus 80 may additionally include an optional radial positioning device (not shown) for manipulating the radial position of member 82 within the patient's esophagus. Apparatus 80 further includes a moveable portion 86, which is selectively displaceable in response to a displacement mechanism, such as a pressure applied to an esophageal lumen 92. In this manner, with apparatus 80 properly positioned within the esophagus, moveable portion 86 will be capable of selectively displacing a wall of the esophagus posterior-laterally in the direction of a portion of the thoracic aorta, such as the descending aorta. Apparatus 80 further includes a heat transfer surface 88 on moveable portion 86, which engages a portion of the wall of the esophagus in the direction of the descending aorta. A pair of tubes 90a, 90b circulate a fluid in thermal contact with heat transfer surface 88 in order to transfer heat between surface 88 and a heat source or sink 70. Apparatus 80 may further include a stomach lumen 94 in order to selectively enlarge an anchoring stomach bladder 84. Tubular member 82 may be extruded of a semi-rigid polymer with heat exchange tubes 90a and 90b, as well esophageal lumen 92 and stomach lumen 94 formed therein, as illustrated in FIG. 15. An optional lumen 96 may be formed in tube 82 in order to provide for venting and/or suction of the stomach.

Apparatus 80 is capable of transferring heat to, or from, the blood flowing through the descending aorta of the patient concurrently with partial occlusion of the descending aorta in order to increase cerebral and myocardial perfusion. While apparatus 80 is also capable of producing substantially complete occlusion of the descending aorta, it is not expected that full occlusion would be useful in combination with a manipulation of the cerebral or core temperature, because the lack of blood flow through the descending aorta would decrease the ability to transfer heat to or from the body.

Figure 17:
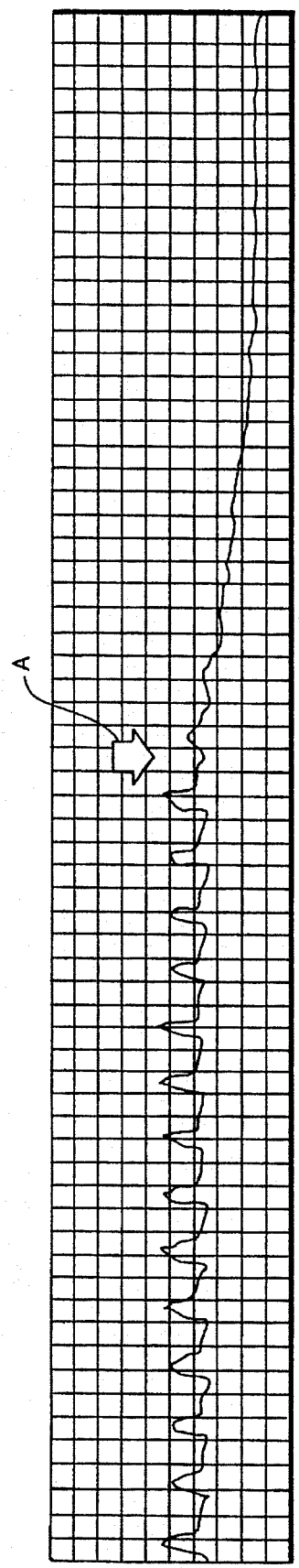
FIG. 17 is a femoral artery pressure diagram of an experimental animal bleeding from the opposite femoral artery illustrating the result achieved by the invention.
Figure 18:
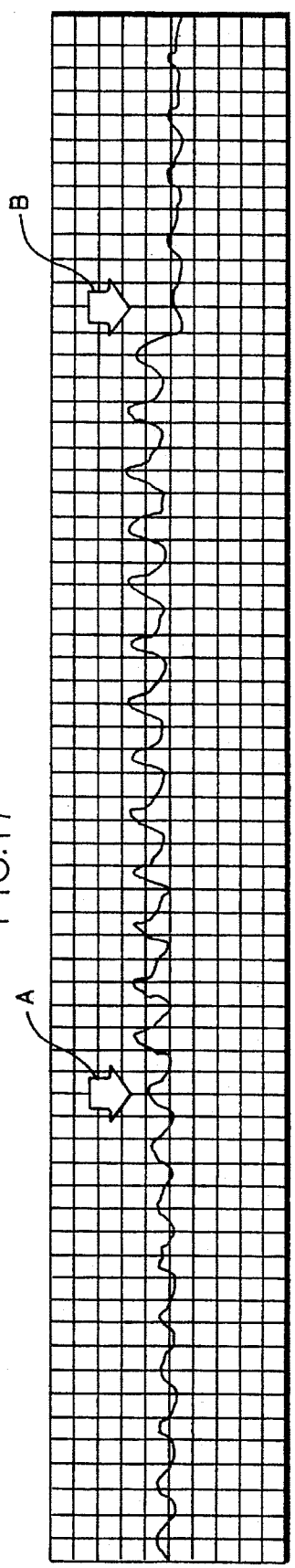
FIG. 18 is a carotid artery pressure diagram made concurrently with the diagram in FIG. 17.
Figure 19:
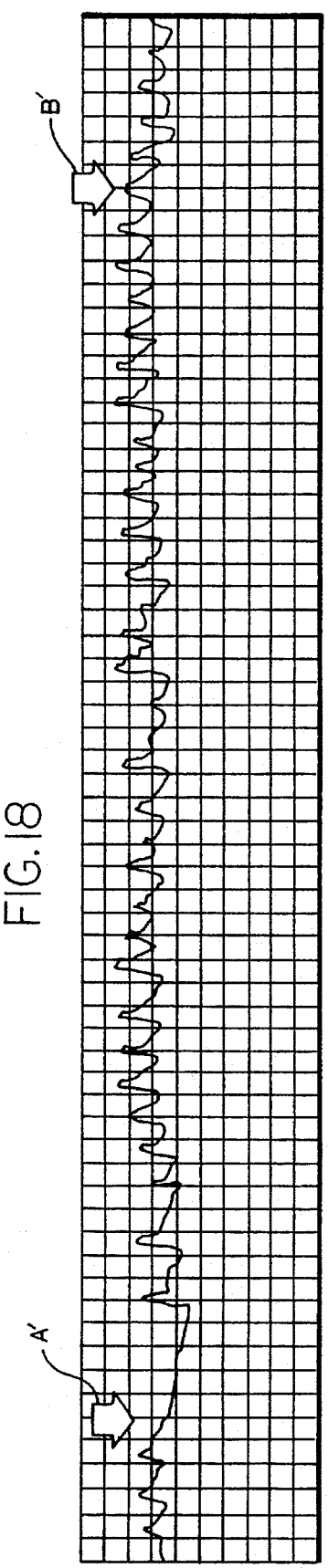
FIG. 19 is a carotid artery pressure diagram of an experimental animal illustrating operation of the invention after resuscitation from a 20-minute cardiac arrest.

Experimental verification of the efficacy of the invention may be seen by reference to FIGS. 17–19. In FIG. 17, a femoral artery pressure signal taken from an animal who is allowed to bleed from the opposite femoral artery illustrates the decrease in femoral artery pressure at A concurrently with initiation of bleeding in the animal. The apparatus was applied to the animal at A in order to cause substantially complete occlusion of the descending thoracic aorta. FIG. 18 illustrates the increase in carotid arterial pressure, beginning at point A, concurrently with the decrease in femoral arterial pressure of the animal. This indicates that the hemorrhage is controlled while preserving or increasing myocardial and cerebral perfusion. The decrease in carotid artery pressure upon disengagement of the apparatus is seen at point B. FIG. 19 illustrates the effect on cerebral and myocardial perfusion during a cardiac arrest. The apparatus is applied to the animal at A' upon resuscitation and ROSC after a 20-minute cardiac arrest. After engaging, the carotid artery pressure increases from 80/50 mm Hg to 120/70 mm Hg. The apparatus is disengaged at B' and the carotid arterial pressure drops back to previous levels. This illustrates that cerebral and myocardial perfusion can be enhanced in the post-resuscitative hypotensive subject and that the effect can be immediately reversed.

During cardiopulmonary resuscitation (CPR), an apparatus 20, 20', 20", 20''' is inserted orally or nasally into the esophagus. The optional stomach bladder is inflated and the displacement mechanism is operated in order to cause maximum impingement of the descending aorta near its beginning. This serves to cause an entirely selective increase in aortic systolic and aortic diastolic pressure without any concomitant change in central venous or intracranial venous pressures. This, in turn, causes a non-pharmacologic rapid increase in coronary and cerebral perfusion pressure and, thus, myocardial and cerebral blood flow. Simultaneous with this increase in perfusion pressure, the core and cerebral temperatures may be lowered with apparatus 80 by circulating cooling fluid through the tubes extending to the heat transfer surface. Once return of spontaneous circulation occurs, selective cerebral hyperperfusion, via selective hypertension, can be maintained for a determined length of time if desired to help prevent post-resuscitation cerebral hypoperfusion. Depending on the state of the myocardium at the time of return of spontaneous circulation (ROSC), the moveable portion may partially impinge the descending aorta to various degrees, allowing partial return of flow through the descending aorta. The apparatus may be synchronized with ventricular contractions, as illustrated in FIG. 16, in order to provide a counter-pulse pump during ventricular diastole in order to simulate intra-aortic balloon pumping. In states of cardiogenic shock, as occur with myocardial infarction, post-cardiac arrest states, various forms of myocarditis, and other forms of myocardial injury, apparatus 20, 20', 20", 20''', 80 may be placed and engaged to cause immediate increase in myocardial and cerebral perfusion to prevent or reverse an agonal state. The moveable portion of the apparatus may be displaced intermittently or during ventricular diastole, as synchronized with the electrocardiogram, to provide counter-pulse pumping. Apparatus 20, 20', 20", 20''', 80 can also be used in the same manner in septic and neurogenic shock as a way to immediately preserve or enhance myocardial and cerebral blood flow until other definitive therapies can be carried out.

Patients with isolated head injuries or head injuries with concomitant extra-cerebral organ system injury may be treated by inserting apparatus 20, 20', 20", 20''', 80 and by displacing the moveable portion to cause various degrees of aortic impingement, thus causing preferential increase in mean arterial pressure to promote greater myocardial and cerebral blood flow. In addition, if therapeutic hypothermia is thought to be beneficial in a particular case, a cold fluid may be circulated through tubes 90a, 90b to the heat transfer surface 88 to reduce cerebral temperatures using apparatus 80. Such application may be particularly helpful in head injury when other organs are injured, such as those in the abdomen in which aortic impingement would reduce hemorrhage while maintaining blood flow to the critically injured brain. While not reducing intracranial pressure, cerebral perfusion pressure is maintained or increased by diverting flow proximal from the point of aortic impingement until other definitive means of reducing intracranial pressure and maintaining cerebral blood flow can be instituted.

Patients with various forms of temperature extremes, such as hypothermia or hyperthermia, may be rapidly brought to states of normothermia by placement of apparatus 60, 60', 80 in the esophagus and transfer of heat to or from the blood flowing through the descending thoracic aorta in order to change the core temperature appropriately. If the patient concomitantly is in the state of shock, moveable portion 86 of apparatus 80 may be displaced to cause various degrees of aortic impingement to preserve myocardial and cerebral blood flow until the state of shock can more definitively be corrected.

Patients who are victims of trauma who do not respond to initial therapies of oxygenation and volume loading, may have apparatus 20, 20', 20", 20''', 80 placed into the esophagus orally or nasally. For victims of trauma who are thought to be hemorrhaging into the abdominal compartment or pelvis, the moveable portion may be extended to cause complete occlusion of the descending thoracic aorta. This, in turn, would reduce the amount of blood flow to the injured compartment, thus reducing blood loss. At the same time, myocardial and cerebral perfusion are maintained or increased. The moveable portion is displaced until formal control of hemorrhage can be obtained at operation or until sufficient volume replacement has taken place. If the patient is hypothermic, warm fluid may be circulated through tubes 90a, 90b of apparatus 80 to increase the patient's core body temperature. The moveable portion may be intermittently retracted if blood flow to the spinal cord is thought to be compromised.

Thus, it is seen that the present invention comprehends a non-invasive technique for occluding the descending aorta and manipulating cerebral and core temperatures by transferring heat to or from blood flowing through the descending aorta and other thoracic vessels and heart. The invention is based upon the realization that the majority of the population has the same relationship of the esophagus to the descending thoracic aorta. The present invention has the ability to cause immediate increase in aortic diastolic pressure in the aortic arch without increasing venous pressure. This, in turn, causes an immediate increase in myocardial and cerebral perfusion. The present invention provides an effect which is immediately reversible. The invention is useful during hemorrhagic shock for its ability to decrease blood loss. The invention is capable of extending the critical time from injury to definitive treatment because it is readily useable by emergency care workers in the field prior to, and during, transport of the patient to appropriate medical facilities. The invention may be used by itself or in combination with other interventions, such as mechanical cardiopulmonary resuscitation (CPR).

The invention effectively causes cerebral hypertension upon return of spontaneous circulation (ROSC), thus helping to reduce the no-reflow and hypoperfusion phenomena, by perhaps preventing sludging in the cerebral microcirculation. The invention further effectively maintains myocardial and cerebral perfusion in the unstable ROSC state until more definitive monitoring and therapy can be instituted. The invention may provide a counter-pulse pump, during a counter-pulsation mode, which impinges the descending thoracic aorta to a varying degree in order to maintain optimal post-ROSC myocardial and cerebral blood flow.

The invention is useful to produce and maintain a state of therapeutic hypothermia to improve neurological outcome. Such states of hypothermia may be readily reversed by the device, if necessary. The invention may produce normalization of body temperature from extremes of hypothermia or hyperthermia while supporting myocardial and cerebral perfusion pressure and flow by various degrees of aortic impingement.

During the treatment of cardiogenic, septic, or neurogenic shock, the invention provides for a counter-pulsation mode or various steady-states of aortic impingement to optimize myocardial and cerebral blood flow to prevent cardiac arrest or cerebral damage until more definitive means of treatment are instituted. The invention further provides for the optimization of core temperature during treatment, if indicated.

The invention allows for the treatment of head injury by providing various degrees of aortic impingement, to redistribute and optimize cerebral blood flow in the face of mounting increases in intracranial pressure, or blood loss from extra-cerebral organ injury. Therapeutic cerebral hypothermia may be instituted, if needed.

In instances of exsanguinating hemorrhagic shock from various causes (trauma, aneurysms and the like) especially below the diaphragm, an apparatus, according to the invention, may be engaged to greatly reduce or stop blood pressure and blood flow below the point of aortic impingement in order to reduce the amount of blood loss. While reducing the amount of blood loss from injuries distal to the point of impingement, myocardial and cerebral perfusion pressure and flow is maintained or enhanced. Impingement can be sequentially reduced to various degrees to allow judgment as to the effectiveness of ongoing volume replacement effort or other efforts to control hemorrhage. Core and cerebral temperatures may be manipulated, according to the invention, to optimize therapy.

Changes and modifications in the specifically described embodiments can be carried out without departing from the principles of the invention. In addition to the fluid and mechanical actuators disclosed herein, other forms of actuation, such as electrical and micro-mechanical actuators, may be utilized. Furthermore, heat may be transferred to blood flowing through other thoracic vessels, such as through the patient's heart, carotid arteries and aortic arch. The protection afforded the invention is intended to be limited only by the scope of the appended claims, as interpreted according to the principles of patent law, including the doctrine of equivalents.

The embodiments of the invention in which an exclusive property or privilege is claimed are defined as follows:

1. A non-invasive method of at least partially occluding the descending thoracic aorta and manipulating core and cerebral temperature of a portion of a patient, including:

positioning in the patient's esophagus a device adapted to extend in said esophagus and selectively displacing with said device a wall of said esophagus posterior-laterally in the direction of said descending thoracic aorta; and exchanging heat between said device and blood flowing through a thoracic vessel in order to increase or decrease the temperature of said blood flowing through said thoracic vessel.

2. The method of claim 1 including displacing said wall sufficiently to cause substantially complete occlusion of said descending aorta.

3. The method of claim 1 wherein said exchanging heat includes circulating a fluid through said device, said fluid having a temperature that is different from the temperature of said blood flowing through said thoracic vessel and exchanging heat between said fluid and said blood flowing through said thoracic vessel.

4. The method of claim 1 wherein said exchanging heat includes pumping heat through said device between said blood flowing through said thoracic vessel and tissue surrounding another portion of said esophagus.

5. The method of claim 1 including displacing said wall of said esophagus in synchronism with the patient's ventricular contraction in order to counter-pulse the descending thoracic aorta during ventricular diastole.

6. The method of claim 1 wherein said thoracic vessel includes one of the patient's descending thoracic aorta, carotid artery, aortic arch, and heart.

7. A non-invasive method of enhancing cerebral and myocardial perfusion in a patient, including:

positioning a device having an elongated tubular member in a portion of the patient's esophagus juxtaposed with the patient's descending thoracic aorta; and displacing with said tubular member a wall of said portion of the esophagus posteriorly-laterally in the direction of said descending thoracic aorta in order to at least partially occlude said descending aorta and thereby increase central and intracranial arterial pressure without increasing central and intracranial venous pressure.

8. The method of claim 7 including substantially completely occluding said descending thoracic aorta.

9. The method of claim 7 including displacing said portion in synchronism with the patient's ventricular contractions in order to counter-pulse the descending thoracic aorta during ventricular diastole.

10. The method of claim 7 wherein said tubular member includes a selectively moveable portion at one end thereof that is adapted to displacing said wall in said direction.

11. The method of claim 10 wherein said device further includes a radial positioning member on an opposite end of said tubular member, and further including manipulating said positioning member in order to radially position said moveable portion to displace in said direction.

12. The method of claim 7 further including monitoring said patient in order to determine the amount of occlusion of the patient's aorta.

13. The method of claim 12 wherein said monitoring includes determining changes in the patient's blood pressure.

14. The method of claim 12 wherein said monitoring includes determining changes in the metabolic state of the patient's myocardium.

15. The method of claim 7 including exchanging heat between said tubular member and blood flowing through said descending thoracic aorta across walls of said esophagus and said aorta in order to manipulate the patient's cerebral and core temperature.

16. A non-invasive method of treating shock in a patient, including:

positioning a device having an elongated tubular member in a portion of the patient's esophagus juxtaposed with the patient's descending thoracic aorta; and displacing with said tubular member a wall of said portion of the esophagus posteriorly-laterally in the direction of said descending thoracic aorta in order to at least partially occlude said descending thoracic aorta in order to increase central and intracranial arterial pressure and to reduce or stop blood flow in said descending thoracic aorta beyond the point of occlusion.

17. The method of claim 16 including substantially completely occluding said descending aorta.

18. The method of claim 16 including displacing said portion in synchronism with the patient's ventricular contractions in order to counter-pulse the aorta during ventricular diastole.

19. The method of claim 16 wherein said elongated member includes a selectively moveable portion at one end thereof that is adapted to displacing said wall in said direction.

20. The method of claim 19 wherein said device further includes a radial positioning member on an opposite end of said tubular member, and further including manipulating said positioning member in order to radially position said moveable portion to displace in said direction.

21. The method of claim 16 further including monitoring said patient in order to determine the amount of occlusion of the patient's aorta.

22. The method of claim 21 wherein said monitoring includes determining changes in the patient's blood pressure.

23. The method of claim 21 wherein said monitoring includes determining changes in the metabolic state of the patient's myocardium.

24. The method of claim 16 including exchanging heat between said device and blood flowing through a thoracic vessel across walls of said esophagus and said thoracic vessel in order to manipulate the patient's core and cerebral temperature.

25. The method of claim 24 wherein said thoracic vessel includes one of the patient's descending thoracic aorta, carotid artery, aortic arch, and heart.

26. A non-invasive method of manipulating core and cerebral temperature of a patient, including:

positioning in the patient's esophagus a device having a heat transfer surface in a manner that said heat transfer surface is at the juxtaposition with a vessel through which blood is flowing; and exchanging heat between said heat transfer surface and blood flowing through said vessel across said wall of said tube and a wall of said vessel.

27. The method of claim 26 wherein said vessel is one of the patient's descending thoracic aorta, carotid artery, aortic arch and heart.

28. The method of claim 27 wherein said vessel is the patient's descending thoracic aorta.

29. The method of claim 26 including circulating a fluid between said heat transfer surface and at least one of a heat source and a heat sink, in order to modify the temperature of said heat transfer surface to a temperature that is different from the temperature of said blood flowing through said vessel and exchanging heat between said blood and said at least one of a heat source and a heat sink.

30. The method of claim 26 wherein said exchanging heat includes transferring heat between said heat transfer surface and another heat transfer surface on said device away from said vessel.

31. The method of claim 26 wherein said device includes an elongated body with said heat transfer surface at one end thereof and a radial positioning member on an opposite end thereof, and further including manipulating said positioning member in order to radially position said heat transfer surface with respect to said vessel.

32. The method of claim 26 further including at least partially occluding said vessel with said device by displacing the patient's esophagus in the direction of said vessel.

* * * * *